United States Patent
Garcia et al.

(10) Patent No.: US 9,165,108 B2
(45) Date of Patent: Oct. 20, 2015

(54) PROBES AND METHODS FOR DETERMINING THE PRESENCE OR ABSENCE OF GENETIC SEGMENTS

(75) Inventors: David Garcia, Derio (ES); Laureano Simon, Derio (ES); Antonio Martinez, Derio (ES); Jorge Ochoa, Derio (ES); Diego Tejedor, Derio (ES); Monica Lopez, Derio (ES)

(73) Assignee: Progenika Biopharma, S.A., Derio (ES)

( * ) Notice: Subject to any disclaimer, the term of this patent is extended or adjusted under 35 U.S.C. 154(b) by 1091 days.

(21) Appl. No.: 13/161,779

(22) Filed: Jun. 16, 2011

(65) Prior Publication Data

US 2011/0313678 A1 Dec. 22, 2011

(30) Foreign Application Priority Data

Jun. 18, 2010 (EP) .................................... 10166561

(51) Int. Cl.
| | |
|---|---|
| G06F 19/22 | (2011.01) |
| C12Q 1/68 | (2006.01) |
| G06F 19/20 | (2011.01) |
| G06F 19/18 | (2011.01) |
| G06F 19/24 | (2011.01) |

(52) U.S. Cl.
CPC .............. *G06F 19/20* (2013.01); *C12Q 1/6876* (2013.01); *G06F 19/18* (2013.01); *G06F 19/24* (2013.01)

(58) Field of Classification Search
CPC ........... C12Q 2600/156; C12Q 1/6827; C12Q 1/6876; C12Q 2525/161; C12Q 1/6813; C12Q 1/6874; G06F 19/18; G06F 19/22; G06F 19/24; G06F 19/20
See application file for complete search history.

(56) References Cited

FOREIGN PATENT DOCUMENTS

WO WO 2006/075254 7/2006

OTHER PUBLICATIONS

Kohara et al. DNA probes on beads arrayed in a capillary, 'Bead-array', exhibited high hybridization performance Nucleic Acids Research vol. 30, article e87 (2002).*
Di et al., "Dynamic model based algorithms for screening and genotyping over 100K SNPs on oligonucleotide microarrays," *Bioinformatics*, vol. 21, No. 9, pp. 1958-1963, 2005.
Liu et al., "Algorithms for large-scale genotyping microarrays," *Bioinformatics*, vol. 19, No. 18, pp. 2397-2403, 2003.
Liu et al., "Rank-based algorithms for analysis of microarrays," *Proc. SPIE*, vol. 4266, pp. 57-67, 2001.
Affymetrix, Inc., "Statistical Algorithms Reference Guide," 2001 (12 pages).
Bolstad et al., "A comparison of normalization methods for high density oligonucleotide array data based on variance and bias," *Bioinformatics*, vol. 19, No. 2, pp. 185-193, 2003.
He and Zhou, "Empirical Evaluation of a New Method for Calculating Signal-to-Noise Ratio for Microarray Data Analysis," *Applied and Environmental Microbiology*, vol. 74, No. 10, pp. 2957-2966, 2008.
Zhao et al., "Microarray analysis of gene expression after transverse aortic constriction in mice," *Physiological Genomics*, vol. 19, pp. 93-105, 2004.
Affymetrix, Inc., "Statistical Algorithms Reference Guide," 2007 (8 pages).

* cited by examiner

*Primary Examiner* — John S Brusca
(74) *Attorney, Agent, or Firm* — Klarquist Sparkman, LLP

(57) ABSTRACT

A method for determining the presence or absence of a genetic segment of interest, such as an exon, an intron or a promoter, in a DNA-containing sample, and probe sets for use in such methods, including probe sets comprising oligonucleotide probes having nucleotides sequences selected from those of SEQ ID NOS: 1-101.

25 Claims, 4 Drawing Sheets

SEQUENCE LISTING

<160> NUMBER OF SEQ ID NOS: 129

<210> SEQ ID NO 1
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 1
cctgcccctc tgggccctaa cactg                                    25

<210> SEQ ID NO 2
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 2
cctgcccctc tgagccctaa cactg                                    25

<210> SEQ ID NO 3
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 3
cctgcccctc tgagcactaa cactg                                    25

<210> SEQ ID NO 4
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 4
cctgcccctc tgcgacctaa cactg                                    25

<210> SEQ ID NO 5
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 5
cctgcccctc tgcgcactaa cactg                                    25

<210> SEQ ID NO 6
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 6
ggtcatcaca ctgttcaggt att                                      23

<210> SEQ ID NO 7
<211> LENGTH: 25
<212> TYPE: DNA
<213> ORGANISM: Artificial sequence

```
<220> FEATURE:
<223> OTHER INFORMATION: Synthetic oligonucleotide probe

<400> SEQUENCE: 7
tggtcatcac actgttcagg tattg                                            25

<210> SEQ ID NO 8
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 8
ggtcatcaca ccgttcaggt att                                              23

<210> SEQ ID NO 9
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 9
tggtcatcac accgttcagg tattg                                            25

<210> SEQ ID NO 10
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 10
gtcatcacac tgttcaggta ttg                                              23

<210> SEQ ID NO 11
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 11
gtcatcacac ttcaggtatt ggg                                              23

<210> SEQ ID NO 12
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 12
cccagtattc ggctggccac catga                                            25

<210> SEQ ID NO 13
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 13
ccagtattcg gctggccacc atg                                              23
```

```
<210> SEQ ID NO 14
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 14
cccagtattc ggtggccacc atgag                                            25

<210> SEQ ID NO 15
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 15
ccagtattcg gtggccacca tga                                              23

<210> SEQ ID NO 16
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 16
aggtgacagc tttaggcaac ctgag                                            25

<210> SEQ ID NO 17
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 17
aggtgacagc ttaggcaacc tgagg                                            25

<210> SEQ ID NO 18
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 18
acatgaacat gatgcacatc tacgt                                            25

<210> SEQ ID NO 19
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 19
catgaacatg atgcacatct acg                                              23

<210> SEQ ID NO 20
<211> LENGTH: 25
<212> TYPE: DNA
<213> ORGANISM: Artificial sequence
<220> FEATURE:
<223> OTHER INFORMATION: Synthetic oligonucleotide probe
```

```
<400> SEQUENCE: 20
acatgaacat gacgcacatc tacgt                                      25

<210> SEQ ID NO 21
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 21
catgaacatg acgcacatct acg                                        23

<210> SEQ ID NO 22
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 22
aacatgatgc acatctacgt gttcg                                      25

<210> SEQ ID NO 23
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 23
acatgatgca catctacgtg ttc                                        23

<210> SEQ ID NO 24
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 24
aacctgaggc acttctacgt gttcg                                      25

<210> SEQ ID NO 25
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 25
acctgaggca cttctacgtg ttc                                        23

<210> SEQ ID NO 26
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 26
aggaagaatg ccgtgttcaa cac                                        23

<210> SEQ ID NO 27
```

```
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 27
aggaagaatg cgtgttcaac acc                                              23

<210> SEQ ID NO 28
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 28
ggctcacccc caagggaagg gaaga                                            25

<210> SEQ ID NO 29
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 29
ggctcacccc cagggaaggg aagat                                            25

<210> SEQ ID NO 30
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 30
atggtgttct ctctctacct tgctt                                            25

<210> SEQ ID NO 31
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 31
tggtgttctc tctctacctt gct                                              23

<210> SEQ ID NO 32
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 32
atggtgttct ctaccttgct tcctt                                            25

<210> SEQ ID NO 33
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 33
```

-continued

```
tggtgttctc taccttgctt cct                                              23

<210> SEQ ID NO 34
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 34
tttgcagact tatgtgcaca gtgcg                                            25

<210> SEQ ID NO 35
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 35
ttgcagactt atgtgcacag tgc                                              23

<210> SEQ ID NO 36
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 36
tttgcagact taggtgcaca gtgcg                                            25

<210> SEQ ID NO 37
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 37
ttgcagactt aggtgcacag tgc                                              23

<210> SEQ ID NO 38
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 38
tttgcagact taagtgcaca gtgcg                                            25

<210> SEQ ID NO 39
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 39
ttgcagactt aagtgcacag tgc                                              23

<210> SEQ ID NO 40
<211> LENGTH: 23
<212> TYPE: DNA
```

<213> ORGANISM: Artificial sequence
<220> FEATURE:
<223> OTHER INFORMATION: Synthetic oligonucleotide probe

<400> SEQUENCE: 40
gcagacttat gtgcacagtg cgg                                    23

<210> SEQ ID NO 41
<211> LENGTH: 21
<212> TYPE: DNA
<213> ORGANISM: Artificial sequence
<220> FEATURE:
<223> OTHER INFORMATION: Synthetic oligonucleotide probe

<400> SEQUENCE: 41
cagacttatg tgcacagtgc g                                      21

<210> SEQ ID NO 42
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 42
gcagacttat gggcacagtg cgg                                    23

<210> SEQ ID NO 43
<211> LENGTH: 21
<212> TYPE: DNA
<213> ORGANISM: Artificial sequence
<220> FEATURE:
<223> OTHER INFORMATION: Synthetic oligonucleotide probe

<400> SEQUENCE: 43
cagacttatg ggcacagtgc g                                      21

<210> SEQ ID NO 44
<211> LENGTH: 21
<212> TYPE: DNA
<213> ORGANISM: Artificial sequence
<220> FEATURE:
<223> OTHER INFORMATION: Synthetic oligonucleotide probe

<400> SEQUENCE: 44
ttggcaggag gcgtggctgt g                                      21

<210> SEQ ID NO 45
<211> LENGTH: 19
<212> TYPE: DNA
<213> ORGANISM: Artificial sequence
<220> FEATURE:
<223> OTHER INFORMATION: Synthetic oligonucleotide probe

<400> SEQUENCE: 45
acagccacgc ctcctgcca                                         19

<210> SEQ ID NO 46
<211> LENGTH: 21
<212> TYPE: DNA
<213> ORGANISM: Artificial sequence
<220> FEATURE:
<223> OTHER INFORMATION: Synthetic oligonucleotide probe

<400> SEQUENCE: 46
ttggcaggag acgtggctgt g                                      21

<210> SEQ ID NO 47
<211> LENGTH: 19
<212> TYPE: DNA
<213> ORGANISM: Artificial sequence
<220> FEATURE:
<223> OTHER INFORMATION: Synthetic oligonucleotide probe

<400> SEQUENCE: 47
acagccacgt ctcctgcca                                              19

<210> SEQ ID NO 48
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 48
gcgtggctgt gggtacctcg tgtca                                       25

<210> SEQ ID NO 49
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 49
cgtggctgtg ggtacctcgt gtc                                         23

<210> SEQ ID NO 50
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 50
gcgtggctgt ggatacctcg tgtca                                       25

<210> SEQ ID NO 51
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 51
cgtggctgtg gatacctcgt gtc                                         23

<210> SEQ ID NO 52
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 52
ggctgtgggt acctcgtgtc acc                                         23

<210> SEQ ID NO 53
<211> LENGTH: 21
<212> TYPE: DNA
<213> ORGANISM: Artificial sequence
<220> FEATURE:

<223> OTHER INFORMATION: Synthetic oligonucleotide probe

<400> SEQUENCE: 53
gctgtgggta cctcgtgtca c        21

<210> SEQ ID NO 54
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 54
ggctgtgggt atctcgtgtc acc        23

<210> SEQ ID NO 55
<211> LENGTH: 21
<212> TYPE: DNA
<213> ORGANISM: Artificial sequence
<220> FEATURE:
<223> OTHER INFORMATION: Synthetic oligonucleotide probe

<400> SEQUENCE: 55
gctgtgggta tctcgtgtca c        21

<210> SEQ ID NO 56
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 56
tgggtacctc gtgtcacctg atccc        25

<210> SEQ ID NO 57
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 57
gggtacctcg tgtcacctga tcc        23

<210> SEQ ID NO 58
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 58
tgggtacctc gtatcacctg atccc        25

<210> SEQ ID NO 59
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 59
gggtacctcg tatcacctga tcc        23

<210> SEQ ID NO 60
<211> LENGTH: 21
<212> TYPE: DNA
<213> ORGANISM: Artificial sequence
<220> FEATURE:
<223> OTHER INFORMATION: Synthetic oligonucleotide probe

<400> SEQUENCE: 60
ggcttgccat ggtgctgggt c                                              21

<210> SEQ ID NO 61
<211> LENGTH: 19
<212> TYPE: DNA
<213> ORGANISM: Artificial sequence
<220> FEATURE:
<223> OTHER INFORMATION: Synthetic oligonucleotide probe

<400> SEQUENCE: 61
gcttgccatg gtgctgggt                                                 19

<210> SEQ ID NO 62
<211> LENGTH: 21
<212> TYPE: DNA
<213> ORGANISM: Artificial sequence
<220> FEATURE:
<223> OTHER INFORMATION: Synthetic oligonucleotide probe

<400> SEQUENCE: 62
ggcttgccat tgtgctgggt c                                              21

<210> SEQ ID NO 63
<211> LENGTH: 19
<212> TYPE: DNA
<213> ORGANISM: Artificial sequence
<220> FEATURE:
<223> OTHER INFORMATION: Synthetic oligonucleotide probe

<400> SEQUENCE: 63
gcttgccatt gtgctgggt                                                 19

<210> SEQ ID NO 64
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 64
gtggctgggc tgatctccgt cgg                                            23

<210> SEQ ID NO 65
<211> LENGTH: 21
<212> TYPE: DNA
<213> ORGANISM: Artificial sequence
<220> FEATURE:
<223> OTHER INFORMATION: Synthetic oligonucleotide probe

<400> SEQUENCE: 65
tggctgggct gatctccgtc g                                              21

<210> SEQ ID NO 66
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 66
gtggctgggc ttggctgatc tcc                                          23

<210> SEQ ID NO 67
<211> LENGTH: 21
<212> TYPE: DNA
<213> ORGANISM: Artificial sequence
<220> FEATURE:
<223> OTHER INFORMATION: Synthetic oligonucleotide probe

<400> SEQUENCE: 67
tggctgggct tggctgatct c                                            21

<210> SEQ ID NO 68
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 68
ggctgatctc cgtcggggga gcc                                          23

<210> SEQ ID NO 69
<211> LENGTH: 21
<212> TYPE: DNA
<213> ORGANISM: Artificial sequence
<220> FEATURE:
<223> OTHER INFORMATION: Synthetic oligonucleotide probe

<400> SEQUENCE: 69
gctgatctcc gtcgggggag c                                            21

<210> SEQ ID NO 70
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 70
ggctgatctc catcggggga gcc                                          23

<210> SEQ ID NO 71
<211> LENGTH: 21
<212> TYPE: DNA
<213> ORGANISM: Artificial sequence
<220> FEATURE:
<223> OTHER INFORMATION: Synthetic oligonucleotide probe

<400> SEQUENCE: 71
gctgatctcc atcgggggag c                                            21

<210> SEQ ID NO 72
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 72
ggagccaagt acctgccggt aag                                          23

<210> SEQ ID NO 73
<211> LENGTH: 21

```
<212> TYPE: DNA
<213> ORGANISM: Artificial sequence
<220> FEATURE:
<223> OTHER INFORMATION: Synthetic oligonucleotide probe

<400> SEQUENCE: 73
gagccaagta cctgccggta a                                              21

<210> SEQ ID NO 74
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 74
ggagccaagt aactgccggt aag                                            23

<210> SEQ ID NO 75
<211> LENGTH: 21
<212> TYPE: DNA
<213> ORGANISM: Artificial sequence
<220> FEATURE:
<223> OTHER INFORMATION: Synthetic oligonucleotide probe

<400> SEQUENCE: 75
gagccaagta actgccggta a                                              21

<210> SEQ ID NO 76
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 76
agtacctgcc ggtaagaaac tagac                                          25

<210> SEQ ID NO 77
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 77
gtacctgccg gtaagaaact aga                                            23

<210> SEQ ID NO 78
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 78
agtacctgcc ggaaactaga caact                                          25

<210> SEQ ID NO 79
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 79
```
gtacctgccg gaaactagac aac        23

<210> SEQ ID NO 80
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 80
tgggtctgct tggagagatc atcta        25

<210> SEQ ID NO 81
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 81
gggtctgctt ggagagatca tct        23

<210> SEQ ID NO 82
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 82
tgggtctgct tgaagagatc atcta        25

<210> SEQ ID NO 83
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 83
gggtctgctt gaagagatca tct        23

<210> SEQ ID NO 84
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 84
ctgctggtgc ttgataccgt cggag        25

<210> SEQ ID NO 85
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 85
tgctggtgct tgataccgtc gga        23

<210> SEQ ID NO 86
<211> LENGTH: 25
<212> TYPE: DNA
<213> ORGANISM: Artificial sequence

```
<220> FEATURE:
<223> OTHER INFORMATION: Synthetic oligonucleotide probe

<400> SEQUENCE: 86
ctgctggtgc ttcatactgt ctgga                                              25

<210> SEQ ID NO 87
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 87
tgctggtgct tcatactgtc tgg                                                23

<210> SEQ ID NO 88
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 88
gtctcctgac aggtcagtgt gaggc                                              25

<210> SEQ ID NO 89
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 89
tctcctgaca ggtcagtgtg agg                                                23

<210> SEQ ID NO 90
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 90
gtctcctgac agatcagtgt gaggc                                              25

<210> SEQ ID NO 91
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 91
tctcctgaca gatcagtgtg agg                                                23

<210> SEQ ID NO 92
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 92
gcatttaaac aggtttgctc ctaaa                                              25
```

<210> SEQ ID NO 93
<211> LENGTH: 27
<212> TYPE: DNA
<213> ORGANISM: Artificial sequence
<220> FEATURE:
<223> OTHER INFORMATION: Synthetic oligonucleotide probe

<400> SEQUENCE: 93
tgcatttaaa caggtttgct cctaaat                                27

<210> SEQ ID NO 94
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 94
gcatttaaac agctttgctc ctaaa                                  25

<210> SEQ ID NO 95
<211> LENGTH: 27
<212> TYPE: DNA
<213> ORGANISM: Artificial sequence
<220> FEATURE:
<223> OTHER INFORMATION: Synthetic oligonucleotide probe

<400> SEQUENCE: 95
tgcatttaaa cagctttgct cctaaat                                27

<210> SEQ ID NO 96
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 96
tattttgatg accaagtttt ctgga                                  25

<210> SEQ ID NO 97
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 97
attttgatga ccaagttttc tgg                                    23

<210> SEQ ID NO 98
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 98
tattttgatg actaagtttt ctgga                                  25

<210> SEQ ID NO 99
<211> LENGTH: 23
<212> TYPE: DNA
<213> ORGANISM: Artificial sequence
<220> FEATURE:
<223> OTHER INFORMATION: Synthetic oligonucleotide probe

```
<400> SEQUENCE: 99
attttgatga ctaagttttc tgg                                              23

<210> SEQ ID NO 100
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 100
gatgcttttg cttaaaatcc aacag                                            25

<210> SEQ ID NO 101
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 101
atgcttttgc ttaaaatcc aacag                                             25

<210> SEQ ID NO 102
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 102
agaagtccaa tcgaaaggaa gaatg                                            25

<210> SEQ ID NO 103
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 103
agaagtccaa tctaaaggaa gaatg                                            25

<210> SEQ ID NO 104
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 104
gaagtccaat cgaaaggaag aat                                              23

<210> SEQ ID NO 105
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 105
gaagtccaat ctaaaggaag aat                                              23

<210> SEQ ID NO 106
```

```
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 106
caaggactat caggccacgg ggtca                                              25

<210> SEQ ID NO 107
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 107
caaggactat cagcccacgg ggtca                                              25

<210> SEQ ID NO 108
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 108
tgaccccgtg gcctgatagt ccttg                                              25

<210> SEQ ID NO 109
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 109
tgaccccgtg ggctgatagt ccttg                                              25

<210> SEQ ID NO 110
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 110
ctggccccca ggcgccctct tct                                                23

<210> SEQ ID NO 111
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 111
ctggccccca gtcgccctct tct                                                23

<210> SEQ ID NO 112
<211> LENGTH: 21
<212> TYPE: DNA
<213> ORGANISM: Artificial sequence
<220> FEATURE:
<223> OTHER INFORMATION: Synthetic oligonucleotide probe

<400> SEQUENCE: 112
```

```
ctggccaagt ttcaactctg c                                              21
```

<210> SEQ ID NO 113
<211> LENGTH: 21
<212> TYPE: DNA
<213> ORGANISM: Artificial sequence
<220> FEATURE:
<223> OTHER INFORMATION: Synthetic oligonucleotide probe

<400> SEQUENCE: 113

```
ctggccaagt gtcaactctg c                                              21
```

<210> SEQ ID NO 114
<211> LENGTH: 19
<212> TYPE: DNA
<213> ORGANISM: Artificial sequence
<220> FEATURE:
<223> OTHER INFORMATION: Synthetic oligonucleotide probe

<400> SEQUENCE: 114

```
tggccaagtt tcaactctg                                                 19
```

<210> SEQ ID NO 115
<211> LENGTH: 19
<212> TYPE: DNA
<213> ORGANISM: Artificial sequence
<220> FEATURE:
<223> OTHER INFORMATION: Synthetic oligonucleotide probe

<400> SEQUENCE: 115

```
tggccaagtg tcaactctg                                                 19
```

<210> SEQ ID NO 116
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 116

```
agtttcaact ctgctctgct gagaa                                          25
```

<210> SEQ ID NO 117
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 117

```
agtttcaact ctcctctgct gagaa                                          25
```

<210> SEQ ID NO 118
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 118

```
ctgctctgct gagaagtcca atcga                                          25
```

<210> SEQ ID NO 119
<211> LENGTH: 25
<212> TYPE: DNA

<213> ORGANISM: Artificial sequence
<220> FEATURE:
<223> OTHER INFORMATION: Synthetic oligonucleotide probe

<400> SEQUENCE: 119
ctgctctgct gaaaagtcca atcga                                          25

<210> SEQ ID NO 120
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 120
tgctctgctg agaagtccaa tcg                                            23

<210> SEQ ID NO 121
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 121
tgctctgctg aaaagtccaa tcg                                            23

<210> SEQ ID NO 122
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 122
agaagtccaa tccaaaggaa gaatg                                          25

<210> SEQ ID NO 123
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 123
gaagtccaat ccaaaggaag aat                                            23

<210> SEQ ID NO 124
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 124
ggaagaatgc cgtgttcaac acc                                            23

<210> SEQ ID NO 125
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 125
ggaagaatgc catgttcaac acc                                            23

```
<210> SEQ ID NO 126
<211> LENGTH: 21
<212> TYPE: DNA
<213> ORGANISM: Artificial sequence
<220> FEATURE:
<223> OTHER INFORMATION: Synthetic oligonucleotide probe

<400> SEQUENCE: 126
gaagaatgcc gtgttcaaca c                                              21

<210> SEQ ID NO 127
<211> LENGTH: 21
<212> TYPE: DNA
<213> ORGANISM: Artificial sequence
<220> FEATURE:
<223> OTHER INFORMATION: Synthetic oligonucleotide probe

<400> SEQUENCE: 127
gaagaatgcc atgttcaaca c                                              21

<210> SEQ ID NO 128
<211> LENGTH: 25
<212> TYPE: DNA
<213> ORGANISM: Artificial sequence
<220> FEATURE:
<223> OTHER INFORMATION: Synthetic oligonucleotide probe

<400> SEQUENCE: 128
agaagtccaa tcaaaaggaa gaatg                                          25

<210> SEQ ID NO 129
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 129
gaagtccaat caaaggaag aat                                             23
```

PROBES AND METHODS FOR DETERMINING THE PRESENCE OR ABSENCE OF GENETIC SEGMENTS

CROSS-REFERENCE TO RELATED APPLICATION

This claims the benefit of European Patent Application No. 10166561.0, filed Jun. 18, 2010, which is incorporated herein in its entirety.

FIELD OF THE INVENTION

The present invention relates to products, in particular probes, and methods for determining the presence or absence of one or more functional genetic segments. Methods for selecting, optimising and using oligonucleotide probes in the determination of the presence or absence of one or more functional genetic segments are disclosed.

BACKGROUND OF THE INVENTION

Determination of the presence or absence of a functional genetic segment in a sample or individual is of great importance in several fields, from forensics, to systematics, to diagnostics and health management. For example, deletions involving tumor suppressor genes are believed to play an important role in the development of several types of cancer (Dutrillaux et al., 1990; Hensel et al., 1990). In the case of human blood groups, absence of certain segments has great implications for blood group phenotypes, which in turn has an effect on transfusion compatibility. For example, Human RhDel is caused by a deletion of 1,013 bp which includes exon 9 of the RHD gene (Chang et al. 1998).

A number of methods are known and used to assess the presence or absence of specific genetic segments. These include sequencing—(Sanger and Coulson, 1975; Smith et al., 1986) based approaches (Kitano et al., 2000) as well as the use of electrophore or Southern blotting (Southern, 1975) to detect markers such as restriction fragment length polymorphisms (RFLP, Botstein et al., 1980) or other markers based on the polymerase chain reaction (PCR, Mullis et al., 1986; Mullis and Faloona, 1987), such as amplicons from sequence-specific primers (Olerup and Zetterquist, 1992) or single-stranded conformational polymorphisms of PCR products (Jin et al. 1993).

Several patents and/or patent applications describe as well methods for detecting absence or deletions of certain functional genetic segments, or their use for certain objectives. For instance, patent application WO 2010/008071 discloses a method for screening the presence or absence of an exon having any gene mutation therein. The method is a gene mutation screening method utilizing a quantitative PCR technique. U.S. Pat. No. 6,599,701 provides methods for characterizing organisms by identifying the presence, absence, size, or sequence polymorphism of intronic regions. WO 2001/018245 provides methods of identifying an alteration in a gene of interest, particularly in the major histocompatibility region, utilizing long range polymerase chain reaction (LR-PCR) amplification of target DNA that includes all or a portion of a human mobile element.

The present invention aims at providing methods for the selection and use of probe sets that allow detecting the presence or absence of functional segments and also in certain cases, both to detect allelic variants located within their cognate sequences and to determine the presence or absence of functional segments simultaneously, in a high-through put way.

DISCLOSURE OF THE INVENTION

Broadly, the present invention provides methods and products for determining the presence or absence of a genetic segment of interest, such as an exon, an intron or a promoter, in a DNA-containing sample. The present inventors have found that a set of probes that interrogate sequences of interest within the genetic segment of interest may be employed in a training step using a plurality of reference samples of known present/absent status, which training step establishes "no call" boundaries that allow subsequent classification of samples as "present" or "absent" with a high degree of statistical confidence. In some cases, the probes include allele-specific probes allowing simultaneous determination a genotype at one or more polymorphic sites together with determination of the presence or absence of a genetic segment. The methods of the invention may thereby provide considerable efficiency savings in comparison with, for example, full sequencing.

Accordingly, in a first aspect the present invention provides a method for determining the presence or absence of a genetic segment of interest, such as an exon, an intron or a promoter, in a DNA-containing sample, the method comprising:
 (i) bringing at least a first probe set comprising a plurality of replicates of at least one oligonucleotide probe that interrogates a first cognate sequence within said segment of interest into contact with (a) a plurality of reference samples in which the genetic segment of interest is absent, and (b) a plurality of reference samples in which the genetic segment of interest is present, under conditions that allow probe-cognate sequence hybridisation to occur;
 (ii) measuring the intensity of probe-sample hybridisation of each of the reference samples, thereby obtaining a first cluster of hybridisation intensity values for the reference samples in which the genetic segment of interest is absent and a second cluster of hybridisation intensity values for the reference samples in which the genetic segment of interest is present; and
 (iii) establishing a "no call" region of hybridisation intensity values that lies in the region between said first and second clusters and which is bounded by a lower no call boundary ("$L_{NC}$") and an upper no call boundary ("$U_{NC}$"), wherein the $L_{NC}$ and $U_{NC}$ represent statistical confidence limits for assigning a hybridisation intensity value to said first and said second clusters, respectively;
 iv) contacting the first probe set with at least one DNA-containing test sample under conditions that allow probe-cognate sequence hybridisation to occur;
 v) measuring the intensity of probe-sample hybridisation of the at least one test sample; and
 vi) comparing the measured hybridisation intensity with the $L_{NC}$ and the $U_{NC}$,
wherein a measured hybridisation intensity below the $L_{NC}$ indicates that said genetic segment of interest is absent in the test sample and a measured hybridisation intensity above $U_{NC}$ indicates that said genetic segment of interest is present in the test sample.

In some cases in accordance with the method of the present invention the cognate sequence comprises a polymorphic site and wherein said first probe set comprises a plurality of replicates of at least two, at least three or at least four allele-specific oligonucleotide probes that distinguish the alleles of said polymorphic site. In particular, the said first probe set may comprise an allele-specific oligonucleotide probe that is exactly complementary to one allele (i.e. complementary to a cognate sequence spanning said polymorphic site) and which allele-specific oligonucleotide is incompletely complementary to the or another allele (i.e. complementary to a cognate sequence spanning said polymorphic site, but including a mis-match at said polymorphic site). The method of the invention may in some cases comprise determining that said test sample does comprise said genetic segment of interest, the method further comprising genotyping said test sample to identify an allele at said polymorphic site. In this way the method of the present invention may advantageously combine genotyping a one or more polymorphic sites (such as SNPs) in addition to determining whether a genetic segment of interest is present of absent. This may be particularly desirable when, for example, a phenotype of interest is associated with both (i) a particular SNP genotype and/or a particular haplotype, and (ii) the presence or absence of a particular genetic segment (e.g. an exon deletion, an intro deletion, an exon duplication or the like).

In some cases, the method in accordance with the present invention may employ multiple probe sets directed to a plurality of cognate sequences within the genetic segment of interest (e.g. each probe set comprising probes that span a different SNP with the genetic segment). Therefore, in some cases in accordance with the present invention at least a second probe set is employed in addition to said first probe set and wherein the second probe set comprises a plurality of replicates of at least one oligonucleotide probe that interrogates a second cognate sequence within said segment of interest, and the method further comprises establishing a second no call region bounded by $L_{NC}$ and $U_{NC}$ boundaries for the second probe set. Likewise, in some cases, at least a third, fourth, fifth, or even tenth, twentieth probe set is employed in addition to said first and/or second probe set and wherein the further probe sets each comprises a plurality of replicates of at least one oligonucleotide probe that interrogates a further cognate sequence within said segment of interest, and the method further comprises establishing a further no call region bounded by $L_{NC}$ and $U_{NC}$ boundaries for each of the further probe sets.

In some cases in accordance with the present invention, the method is for determining the presence or absence of two or more genetic segments (e.g. two or more exons, two of more introns, two or more promoters, and/or any combination of said genetic segments), wherein said steps i) to vi) are carried out for each genetic segment of interest. The genetic segments may be selected from the same gene or from a plurality of genes. In some cases, the method of the present invention comprises determining the presence of absence of a plurality of exons of the same gene (e.g. 2, 3, 4, 5, 6, 7, 8, 9 or more exons selected from exons 1-10 of the RHD gene and/or an RHCE gene).

In some cases in accordance with the method of the present invention, the test sample is classified as having or not having said segment of interest based on a strict consensus between the determinations of the first and second probe sets, optionally according to a strict consensus as shown in Table 1. In some cases in accordance with the method of the present invention, the test sample is classified as having or not having said segment of interest based on a majority consensus between the determinations of the first and second probe sets in the absence of contradictory determinations, optionally according to a majority consensus as shown in Table 2.

In some cases in accordance with the method of the present invention, the oligonucleotide probes are attached to a solid support, optionally wherein:
(a) the oligonucleotide probes are attached to a substantially planar solid support in the form of an array; or
(b) the oligonucleotide probes are attached to particles, such as micrometer- or nanometer-sized beads, cylinders or any other particle.

In some cases in accordance with the method of the present invention the test sample comprises DNA amplified from genomic DNA of a test subject, which DNA has optionally been fragmented and/or labelled with a detectable label. In some cases in accordance with the method of the present invention each of the reference samples comprises DNA amplified from genomic DNA of a reference subject, which DNA has optionally been fragmented and/or labelled with a detectable label.

In some cases in accordance with the method of the present invention the DNA of the reference samples and/or the test sample is or has been labelled with a fluorescent label and the method involves measuring hybridisation intensity by measuring the fluorescence signal of the fluorescent label at each oligonucleotide probe location. The intensity of the fluorescence signal may thereby provide a measure of the degree of hybridisation. Indeed, under certain hybridisation conditions, the fluorescence signal provides a measure of how well the labelled fragments derived from the DNA-containing sample bind and hybridise to the respective probe sequences.

In some cases in accordance with the method of the present invention the hybridisation intensity for each probe set is measured as I/B, where:

I is determined as a measure of central tendency, such as mean or median, of the measured fluorescence signal of the replicates of each oligonucleotide probe, optionally after trimming extreme readings; and B is determined as a measure of central tendency, such as mean or median, of the background fluorescence signal of the replicates of each oligonucleotide probe, optionally after trimming extreme readings. As used herein, "trimming extreme readings" may in some cases involve discarding the extreme decile (i.e. the top 10% and the bottom 10% of readings from a set of replicates), the extreme two deciles (i.e. the top 20% and the bottom 20% of readings from a set of replicates) or the top 5% and the bottom 5% of readings from a set of replicates.

In some cases in accordance with the method of the present invention the $L_{NC}$ and $U_{NC}$ values are calculated as follows:

$$L_{NC} = \frac{T_{I/B} \cdot [2 \cdot a(I/B)_n - aMedian\ I/B] - a(I/B)_n^2}{T_{I/B} - aMedian\ I/B}$$

$$U_{NC} = \frac{T_{I/B} \cdot [pMedian\ I/B - 2 \cdot p(I/B)_1] + p(I/B)_1^2}{pMedian\ I/B - T_{I/B}}$$

where:

$$T_{I/B} = \frac{pMedian\ I/B \cdot a(I/B)_n - aMedian\ I/B \cdot p(I/B)_1}{pMedian\ I/B + a(I/B)_n - aMedian\ I/B - p(I/B)_1}$$

aMedianI/B is a measure of central tendency, such as the median or mean, of the measured I/B values of the reference samples in which the genetic segment of interest is absent;

pMedianI/B is a measure of central tendency, such as the median or mean, of the measured I/B values of the reference samples in which the genetic segment of interest is present;

a(I/B)$_n$ is the greatest measured I/B value of the reference samples in which the genetic segment of interest is absent; and p(I/B)$_1$ is the lowest measured I/B value of the reference samples in which the genetic segment of interest is present.

In some cases in accordance with the method of the present invention the genetic segment of interest comprises an exon of the human RHD gene.

In some cases in accordance with the method of the present invention the oligonucleotide probes are selected from the probes shown in Table 4. The probes may in some cases be selected in groups according to the exon to which they are targeted.

In some cases in accordance with the method of the present invention the method further comprises genotyping the test sample to identify at least one allele at a site of single nucleotide polymorphism ("SNP") in the human RHD gene.

In a second aspect the present invention provides a probe set for determining the presence or absence in a DNA-containing test sample of at least one exon of the human RHD gene, the set comprising a plurality of oligonucleotide probes of between 10-50 nucleotides in length, optionally 15-40 or 19-27 nucleotides in length, each of the probes comprising or consisting of a contiguous nucleotide sequence selected from the sequences of SEQ ID NOS: 1-101 shown in Table 4.

In some cases, the probe set in accordance with the invention is for determining the presence or absence in a DNA-containing test sample of at least two exons of the human RHD gene, the set comprising two or more of (i)-(x):
(i) one or more RHD exon 1 probes of SEQ ID NOS: 1-5;
(ii) one or more RHD exon 2 probes of SEQ ID NOS: 6-11;
(iii) one or more RHD exon 3 probes of SEQ ID NOS: 12-17;
(iv) one or more RHD exon 4 probes of SEQ ID NOS: 18-25;
(v) one or more RHD exon 5 probes of SEQ ID NOS: 26-29;
(vi) one or more RHD exon 6 probes of SEQ ID NOS: 30-79;
(vii) one or more RHD exon 7 probes of SEQ ID NOS: 80-87;
(viii) one or more RHD exon 8 probes of SEQ ID NOS: 88-91;
(ix) one or more RHD exon 9 probes of SEQ ID NOS: 92-99; and
(x) one or more RHD exon 10 probes of SEQ ID NOS: 100-101.

In some cases in accordance with the present invention the plurality of oligonucleotide probes of said probe set are attached to a solid support, optionally wherein:
the oligonucleotide probes are attached to a substantially planar solid support in the form of an array; or
the oligonucleotide probes are attached to particles, such as micrometer- or nanometer-sized beads, cylinders or any other particle.

In a third aspect, the present invention provides use of a probe set in accordance with the present invention in a method of the invention.

In a fourth aspect, the present invention provides a kit comprising a probe set in accordance with the present invention and one or more of the following components:
(i) reagents and/or PCR primers suitable for amplifying human genomic DNA that comprises all or part of the RHD gene;
(ii) a fluorescent label suitable for labelling DNA; and
(iii) instructions for performing a method in accordance with the present invention.

In a fifth aspect, the present invention provides a method for selecting at least one optimal probe set for use in a method in accordance with the first aspect of the invention, the method comprising:
(i) providing a plurality of candidate probe sets, each candidate probe set comprising a plurality of replicates of at least one oligonucleotide probe that interrogates a cognate sequence within a genetic segment of interest;
(ii) bringing each of the candidate probe sets into contact with (a) a plurality of reference samples in which the genetic segment of interest is absent, and (b) a plurality of reference samples in which the genetic segment of interest is present, under conditions that allow probe-cognate sequence hybridisation to occur;
(iii) measuring the intensity of probe-sample hybridisation of each of the reference samples, thereby obtaining for each candidate probe set a first cluster of hybridisation intensity values for the reference samples in which the genetic segment of interest is absent and a second cluster of hybridisation intensity values for the reference samples in which the genetic segment of interest is present; and
(iv) scoring each of the candidate probe sets by dividing a measure of the interval between the first and second clusters by the sum of a measure of central tendency of the first and second clusters, thereby obtaining a probe set score for each of the candidate probe sets, wherein a higher probe set score indicates that the candidate probe set is more likely to be optimal for determining the presence or absence of the genetic segment of interest.

In some cases, in accordance with the fifth aspect of the invention, the reference samples are labelled with a fluorescent label and wherein the hybridisation intensity is measured as I/B, where:

I is determined as a measure of central tendency, such as mean or median, of the measured fluorescence signal of the replicates of each oligonucleotide probe, optionally after trimming extreme readings, and B is determined as a measure of central tendency, such as mean or median, of the background fluorescence signal of the replicates of each oligonucleotide probe, optionally after trimming extreme readings, and wherein the probe set score (S) for each candidate probe set is calculated as follows:

$$S = \frac{A}{M} = \frac{p(I/B)_1 - a(I/B)_n}{pMedian\ I/B + aMedian\ I/B}$$

where:
aMedianI/B is a measure of central tendency, such as the median or mean, of the measured I/B values of the reference samples in which the genetic segment of interest is absent;

pMedianI/B is a measure of central tendency, such as the median or mean, of the measured I/B values of the reference samples in which the genetic segment of interest is present;

a(I/B)$_n$ is the greatest measured I/B value of the reference samples in which the genetic segment of interest is absent; and p(I/B)$_1$ is the lowest measured I/B value of the reference samples in which the genetic segment of interest is present.

In some cases in accordance with the first aspect of the invention, at least said first probe set is a probe set that has been selected using a method in accordance with the fifth aspect of the invention.

In a sixth aspect, the present invention provides a method for determining a lower no call boundary ("$L_{NC}$") and an upper no call boundary ("$U_{NC}$") for at least a first probe set, the method comprising:

(i) bringing at least said first probe set comprising a plurality of replicates of at least one oligonucleotide probe that interrogates a first cognate sequence within a genetic segment of interest into contact with (a) a plurality of reference samples in which the genetic segment of interest is absent, and (b) a plurality of reference samples in which the genetic segment of interest is present, under conditions that allow probe-cognate sequence hybridisation to occur;

(ii) measuring the intensity of probe-sample hybridisation of each of the reference samples, thereby obtaining a first cluster of hybridisation intensity values for the reference samples in which the genetic segment of interest is absent and a second cluster of hybridisation intensity values for the reference samples in which the genetic segment of interest is present; and (iii) establishing a "no call" region of hybridisation intensity values that lies in the region between said first and second clusters and which is bounded by $L_{NC}$ and $U_{NC}$, wherein the $L_{NC}$ and $U_{NC}$ represent statistical confidence limits for assigning a hybridisation intensity value to said first and said second clusters, respectively.

In a seventh aspect, the present invention provides a method for determining the presence or absence of a genetic segment of interest in a DNA-containing sample, the method comprising:

(i) bringing at least a first probe set comprising a plurality of replicates of at least one oligonucleotide probe that interrogates a first cognate sequence within said segment of interest into contact with at least one DNA-containing test sample under conditions that allow probe-cognate sequence hybridisation to occur;

(ii) measuring the intensity of probe-sample hybridisation of the at least one test sample; and (iii) comparing the measured hybridisation intensity with a pre-determined $L_{NC}$ and a pre-determined $U_{NC}$, wherein the $L_{NC}$ and the $U_{NC}$ have been determined by a method in accordance with the sixth aspect of the invention, and wherein a measured hybridisation intensity below the $L_{NC}$ indicates that said genetic segment of interest is absent in the test sample and a measured hybridisation intensity above $U_{NC}$ indicates that said genetic segment of interest is present in the test sample.

The present invention includes the combination of the aspects and preferred features described except where such a combination is clearly impermissible or is stated to be expressly avoided. These and further aspects and embodiments of the invention are described in further detail below and with reference to the accompanying examples and figures.

SEQUENCES LISTING

Figure 1A:
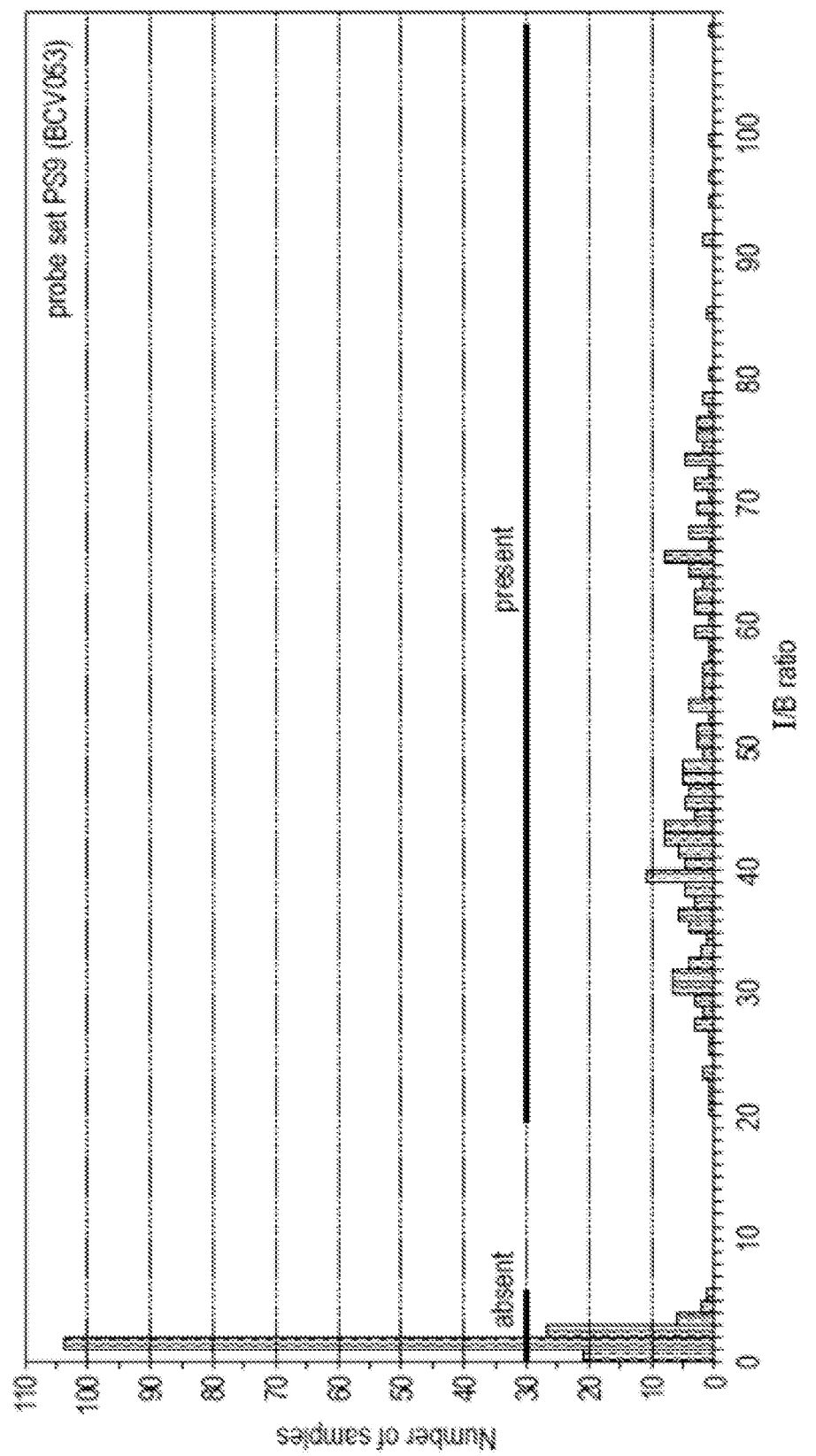
FIGS. 1A and B show the frequency of samples in the reference sample set as a function of their I/B ratio for the optimal probe sets A) PS9 and B) PS11 (Blood Group Genotyping IDs BCV053 and BCV055, respectively). The left-hand bars show those samples in which the RHD exon 5 is absent; the right-hand bars show those in which the RHD exon 5 is present.

The Sequence Listing is submitted as an ASCII text file in the form of the file named Sequence_Listing.txt, which was created on Jun. 15, 2011, and is 26,790 bytes, which is incorporated by reference herein.

DETAILED DESCRIPTION OF THE INVENTION

The present invention relates to a method of genotyping and data analysis for determining the presence or absence of one or more functional segments (e.g. promoter, exon, intron), portions of them, and/or combinations of them, in particular loci of an individual's genomic DNA.

The method makes use of the detection or lack of detection of one or more specific nucleotide sequences within the functional segments. The specific nucleotide sequences, hereafter named cognate sequences, consist usually but not exclusively of stretches of 19-27 base pairs. In some cases, the nucleotide at the central position within the cognate sequence, plays a pivotal role in the detection process, and therefore in the determination of presence versus absence of functional segments.

In certain cases, the method of the invention may be termed Allele-Specific Hybridization, and may make use of synthetic oligonucleotide probes usually 10-50 nucleotides long, preferably 19-27 nucleotides long, the sequences of which are designed to be complementary to the interrogated cognate sequence. Complementarity of sequences enables pairing of genomic DNA and oligonucleotide probe molecules. Specific pairing, i.e. pairing of probes to their cognate sequence and to no other sequence, can be made to occur under appropriate conditions, which include but are not limited to time of incubation, temperature of incubation, concentration of probe and cognate sequences, and mixing. Specific pairing to probes allows detection of cognate sequences in a mix of cognate and non-cognate sequences. Detection or lack of detection of cognate sequences, in turn, allows determination of presence versus absence of functional segments.

Synthetic oligonucleotide probes can be used for the detection of particular conserved, non-variant regions and/or allelic variants in an individual's genomic DNA. Often, allelic variants are single nucleotide polymorphisms (SNPs), i.e. nucleotide positions at which the DNA composition may vary across individuals.

In some cases, the synthetic oligonucleotide probes described herein are designed and used to detect the presence or absence of functional segments and also, both to detect allelic variants located within their cognate sequences and to determine the presence or absence of functional segments.

Given a particular nucleotide at a particular position of a locus of genomic DNA, synthetic oligonucleotide molecules, hereafter referred to as probes, can be designed to detect said nucleotide in a test sample. Probes can be designed in pairs such that one member of the probe pair is complementary to one strand of the cognate sequence, whereas the other member of the probe pair is complementary to the other strand of the cognate sequence. Probes can also be designed in sets so that they have different lengths and be complementary to one strand or the two strands of the cognate sequence. The number of probes used to interrogate a non-variant segment is at least one, and often two or four.

The set of at least one, often two or four, probes that interrogates a cognate sequence is referred to as probe set. Parameters evaluated in the design of probes in order to maximize the sensitivity and specificity of cognate sequence detection are their nucleotide composition, their nucleotide sequence, their length, and the DNA strand to which they are made complementary. Among the designed sequences, the process of probe selection is largely empirical.

SNPs are typically defined by two alternative nucleotides at a single position, where each of the two alternative nucleotides defines one of two allelic variants.

Given a single nucleotide polymorphism (SNP) at a particular position of a locus of genomic DNA, and given two allelic variants A and B defined by the particular nucleotide at said position, probes can be designed in pairs to detect variant A and/or variant B in a test sample. The design is such that one member of the probe pair is complementary in full to one strand of the cognate sequence of allelic variant A, and in part to the cognate sequence of allelic variant B, whereas the other member of the probe pair is complementary in full to the same strand of the cognate sequence of allelic variant B, and in part to the cognate sequence of allelic variant A. In most instances, complementarity in part refers to complementarity at all but the central nucleotide position of the cognate sequence. More than two probes can be designed, so that complementarity is to one or the two strands of the cognate sequence and/or probes have different lengths.

Given that most SNPs consist of two allelic variants, the number of probes used to interrogate a SNP is at least two, and often four. When four probes are used, usually two are made to be complementary to each allelic variant, with each of the two for a given allelic variant being complementary to either DNA strand of the cognate sequence, or with each of the two for a given allelic variant comprising a unique nucleotide length. The set of at least two, usually four probes that interrogates a SNP is referred to as probe set. Parameters evaluated in the design of probes in order to maximize the sensitivity and specificity of cognate sequence detection are their nucleotide composition, their nucleotide sequence, their length, and the DNA strand to which they are made complementary. Among the designed sequences, the process of probe selection is largely empirical.

At least one probe set may be used to interrogate a non-variant segment and/or a SNP, and therefore at least one probe set is used to determine the presence or absence of a functional segment. A genotype determination, i.e. detection or no detection of the functional segment, or detection of the presence or absence of a functional segment, is made from numerical values which are a measure of the abundance of cognate sequences in the test sample. In order to minimise inter-assay variation in the measurement of a single non-variant segment and/or a SNP may, which has the potential to lead to an erroneous determination, it is often desirable to use more than one probe set to make such determination. Use of more than one probe set may help to avoid or minimise the effect of genetic events such as insertions, deletions, conversions, 3D-structures and the like. As contemplated herein, no particular restriction is placed on the location of multiple cognate sequences within a genetic segment of interest, i.e. they can be overlapping or non-overlapping, contiguous or non-contiguous.

In accordance with any aspect of the present invention, probes may be attached to a chemically-functionalized solid support. An example of a solid support is a flat glass surface, on which probe molecules are placed by contact deposition. Another example of a solid support is a micrometer-size polymer bead, to which probe molecules are attached by conjugation. Another example of a solid support is a nanometer-size particle to which probe molecules are attached. An exemplary description herein relates to the procedure performed wherein the probes are immobilised on a flat glass surface. Attachment of a probe to the surface is performed at multiple individual locations (in the case of particles, attachment would be to multiple ensembles of particles), hereafter referred to as replicate features or "replicates". The number of replicate features for each probe is usually ten, although it may vary.

In accordance with any aspect of the present invention, functional segments or their portions encompassing cognate sequences may be amplified, for example by PCR, using as a template genomic DNA in a reference sample and/or in a test sample. Amplified functional segments or their portions can be labeled (e.g. with a fluorescent label) to allow for their detection, and optionally fragmented to facilitate their pairing with oligonucleotide probes.

In accordance with any aspect of the present invention, labelled and fragmented functional segments or their portions may be incubated under conditions that maximize the sensitivity and specificity of pairing with probes attached to the solid support. The amount of probe-paired functional segments or their portions may be determined indirectly from the measurement of label, usually a fluorochrome, attached to the solid support. This measurement is referred to herein as signal intensity. By way of example, the fluorescence emitted by the fluorochrome may be collected by means of a fluorescence detection device, such as a confocal scanner. The signal intensity attached to each probe feature may be quantified by ad hoc software and transformed into numerical values that, for example, may range between 0 and 65,000.

In some cases in accordance with the method of any aspect of the present invention, the raw intensity values from all the probe features that interrogate a cognate sequence may be processed to make a determination as to the presence or absence of a functional segment in the following manner: in a first step, background noise values, if present, (B) are subtracted from signal intensity values (I) for each of the, for example, ten replicate features in order to obtain corrected signal intensity values (C).

$$C_n = I_n - B_n$$

where n takes values between 1 and the number of replicate features, for example 10.

Optionally, in a second step, some, for example one, usually two out of the number of replicate features, for example ten, replicate features $(R_{i1}, R_{i2})$ whose corrected signal intensity values are largest $(C_{i1}, C_{i2})$, and some, for example one, usually two out of the number of replicate features, for example ten replicate features $(R_{i9}, R_{i10})$ whose corrected signal intensity values are smallest $(C_{i9}, C_{i10})$, are removed from the analysis. This step can also be described as "trimming" with a, for example, twenty per cent trim on each end of the data set distribution:

Distribution of Values:
$C_{i1} > C_{i2} > C_{i3} > C_{i4} > C_{i5} > C_{i6} > C_{i7} > C_{i8} > C_{i9} > C_{i10}$
Trimmed Distribution of Values:
$C_{i3} > C_{i4} > C_{i5} > C_{i6} > C_{i7} > C_{i8}$
Discarded Replicate Features:
$R_{i1}, R_{i2}, R_{i9}, R_{i10}$ In a third step, a measure of central tendency, for example arithmetic mean, other means, median for intensity is obtained for a probe set by pooling signal intensity values that correspond to the remaining replicate features. As an example, for a probe set that consists of four probes, i, j, k, l, twenty-four values are averaged, which correspond to the product of six remaining replicate features per probe times four probes.

$$\text{Mean}I = \text{Mean}(I_{i3-i8}, I_{j3-j8}, I_{k3-k8}, I_{l3-l8})$$

In a fourth step, an average background is obtained for a probe set by pooling background noise values (or an equivalent, for example, a measure of central tendency, such as arithmetic mean, other means, median of intensities) that correspond to the remaining replicate features. As in the example above:

$$\text{Mean}B = \text{Mean}(B_{i3-i8}, B_{j3-j8}, B_{k3-k8}, B_{l3-l8})$$

In a fifth step, the signal intensity measure of central tendency, for example arithmetic mean, other means, median is divided by the background noise measure of central tendency, for example arithmetic mean, other means, median in order to obtain an Intensity/Background (I/B) ratio for each probe set, i.e. for each polymorphism.

$$I/B = \text{Mean}I/\text{Mean}B$$

Differences exist among probe sets in the signal intensity and background noise that they detect upon hybridization to their cognate sequences, i.e. in their I/B ratios. Differences also exist among probe sets in the gap or interval between the I/B ratios for a genetic segment when absent versus when present. Differences also exist among probe sets in the extent of variation of their I/B ratios, both across assays and across samples. As a consequence, certain probe sets are better indicators of the presence or absence of a genetic segment than others. Thus, it becomes desirable to select among the probe sets that interrogate non-variant segments and/or SNPs in a given genetic segment those whose I/B ratios best discriminate between the absence and the presence of said segment.

Determination of the presence or absence of a genetic segment in a given sample is performed by assigning said sample to one of two clusters of possible I/B ratios, wherein ranges for possible I/B ratios when the genetic segment in question is present and when the genetic segment in question is absent have been determined previously in a reference sample set for which presence versus absence of a functional segment was known. I/B ratio values for a given sample are compared to a lower I/B boundary ($L_{NC}$) and an upper I/B boundary ($U_{NC}$) of the "No Call" I/B region.

The "No Call" I/B region corresponds to a range of I/B ratios which do not allow the determination of presence versus absence of the genetic segment with sufficient confidence. It is located between the minimum I/B ratio of samples in which the genetic segment is known to be present [$p(I/B)_1$] and the maximum I/B ratio of samples in which the genetic segment is known to be absent [$a(I/B)_n$]. Determination of a lower I/B boundary ($L_{NC}$) and an upper I/B boundary ($U_{NC}$) of the "No Call" I/B region is explained in further detail herein.

The present inventors have found that it is possible to derive $L_{NC}$ and $U_{NC}$ boundaries such that the no call region is smaller than the absolute difference between $p(I/B)_1$ and $a(I/B)_n$, whilst still retaining sufficient statistical confidence to classify an I/B ratio reading of a test sample as "present" or "absent" (see, for example, FIG. 2 in which $L_{NC}$ is greater than $a(I/B)_n$ and $U_{NC}$ is lower than $p(I/B)_1$). Deriving a no call region that is smaller than the absolute difference between $p(I/B)_1$ and $a(I/B)_n$ is advantageous because it allows for the number of ambiguous "no call" readings to be minimised, whilst retaining confidence in readings that are outside the no call region.

Selecting Optimal Probe Sets

The present invention provides a method for selection of optimal probe sets to determine presence versus absence of a genetic segment among those probe sets that interrogate non-variant segments and/or variants located in said genetic segment. In certain cases in accordance with the method of the present invention the selection comprises the following steps.

First, for each probe set a distribution of I/B ratios is created from a sample set of size m in which the genetic segment of interest is known to be present (p), and a distribution of I/B ratios from a sample set of size n in which the genetic segment of interest is known to be absent (a):

$$p(I/B)_1 < p(I/B)_2 < \ldots < p(I/B)_{m-1} < p(I/B)_m$$

$$a(I/B)_1 < a(I/B)_2 < \ldots < a(I/B)_{n-1} < a(I/B)_n$$

Second, for each probe set the amplitude of the interval (A) is calculated by subtracting the largest I/B ratio in the sample set in which the genetic segment of interest is known to be absent from the smallest I/B ratio in the sample set in which the genetic segment of interest is known to be present.

$$A = p(I/B)_1 - a(I/B)_n$$

A can take negative, zero, or (more often) positive values. The power of a probe set to discriminate between absence and presence of the genetic segment correlates with the size of A. Therefore, the process of selection of optimal probe sets favours those sets for which A is maximal.

Based on their larger A, any number of probe sets, often two optimal probe sets can be selected to determine presence versus absence of the genetic segment. The optimal discriminatory power of the selected probe sets may be verified by comparing the selected probe sets with randomly selected pairs of probe sets and/or with all probe sets available within the genetic segment of interest.

Optionally, the following steps can also be performed: Third, for each probe set measure of central tendency, for example arithmetic mean, other means, median is calculated for I/B ratio in the sample set in which the genetic segment of interest is known to be present (pMedian I/B), and the measure of central tendency, for example arithmetic mean, other means, median is calculated for I/B ratio in the sample set in which the genetic segment of interest is known to be absent (aMedian I/B).

$$p\text{Median}I/B = \text{Median}[p(I/B)_1, \ldots, p(I/B)_m]$$

$$a\text{Median}I/B = \text{Median}[a(I/B)_1, \ldots, a(I/B)_n]$$

Fourth, for each probe set the sum of the measure of central tendency, for example arithmetic mean, other means, median is calculated for I/B ratios (M), i.e. the ratio for the sample set in which the genetic segment of interest is known to be present plus the ratio for the sample set in which the genetic segment of interest is known to be absent.

$$M = p\text{Median}I/B + a\text{Median}I/B$$

Since pMedian I/B>0 and aMedian I/B>0, M>0. For probe sets with a given A, the power to discriminate between absence and presence of the genetic segment decreases as M increases. Therefore, the process of selection of optimal probe sets favours those sets for which M is minimal.

Based on their smaller M, any number of probe sets, often two optimal probe sets can be selected to determine presence versus absence of the genetic segment. The optimal discriminatory power of the selected probe sets may be verified by comparing the selected probe sets with randomly selected pairs of probe sets and/or with all probe sets available within the genetic segment of interest.

Optionally, the following step can be performed: Fifth, for each probe set a score (S) is calculated by dividing the amplitude of the interval (A) by the sum of measure of central tendency, for example arithmetic mean, other means, median for I/B ratios (M):

$$S = \frac{A}{M} = \frac{p(I/B)_1 - a(I/B)_n}{pMedian\ I/B + aMedian\ I/B}$$

Since $p(I/B)_1$<pMedian I/B, and since $a(I/B)_n$>aMedian I/B, A<M. Therefore, S takes absolute values between 0 and 1. Since M>0, when A<0, S<0, and when A>0, S>0.

Based on their larger S, any number of probe sets, often two optimal probe sets, are selected to determine presence versus absence of the genetic segment. The optimal discriminatory power of the selected probe sets may be verified by comparing the selected probe sets with randomly selected pairs of probe sets and/or with all probe sets within the genetic segment of interest.

For genetic segments for which no optimal pair of probe sets outperforms randomly selected pairs of probe sets or all probe sets, any one, more than one, or all probe sets can be used to determine presence versus absence of the genetic segment.

Establishing No Call Boundaries

The present invention provides a method for establishing a lower I/B boundary ($L_{NC}$) and an upper I/B boundary ($U_{NC}$) of the "No Call" I/B region.

When the amplitude of the interval (A) mentioned above is positive $$A = p(I/B)_1 - a(I/B)_n$$

, the lower I/B boundary ($L_{NC}$) of the "No Call" I/B region can be equal to the largest I/B ratio in the reference sample set in which the genetic segment of interest is known to be absent ($L_{NC} = a(I/B)_n$); and the upper I/B boundary ($U_{NC}$) of the "No Call" I/B region can be equal to the smallest I/B ratio in the reference sample set in which the genetic segment of interest is known to be present ($U_{NC} = p(I/B)_1$).

Advantageously, the following step can be performed: For each optimal probe set a weighed I/B ratio threshold ($T_{I/B}$) may be calculated.

$T_{I/B}$ is a reference point located between the I/B ratios of the sample set in which the genetic segment of interest is known to be present and the I/B ratios of the sample set in which the genetic segment of interest is known to be absent.

The value of $T_{I/B}$ is determined from the measure of central tendency, for example arithmetic mean, other means, median and minimum I/B ratios of samples in which the genetic segment is known to be present [pMedian I/B, $p(I/B)_1$], and the measure of central tendency, for example arithmetic mean, other means, median and maximum I/B ratios of samples in which the genetic segment is known to be absent [aMedian I/B, $a(I/B)_n$].

Specifically, the value of $T_{I/D}$ may be established to be such that the distances from $T_{I/B}$ to pMedian I/B and aMedian I/B are proportional to the distances from $p(I/B)_1$ and $a(I/B)_n$ to pMedian I/B.

$$\frac{pMedian\ I/B - T_{I/B}}{pMedian\ I/B - p(I/B)_1} = \frac{T_{I/B} - aMedian\ I/B}{a(I/B)_n + aMedian\ I/B}$$

Therefore, $$T_{I/B} = \frac{pMedian\ I/B \cdot a(I/B)_n - aMedian\ I/B \cdot p(I/B)_1}{pMedian\ I/B + a(I/B)_n - aMedian\ I/B - p(I/B)_1}$$

The lower ($L_{NC}$) and the upper ($U_{NC}$) I/B boundaries of the "No Call" I/B region can be equal to the weighed I/B ratio threshold ($T_{I/B}$).

Optionally, the following further step can be performed: First, for each optimal probe set the upper boundary of the "No Call" I/B region ($U_{NC}$) is calculated.

The "No Call" I/B region corresponds to a range of I/B ratios which do not allow the determination of presence versus absence of the genetic segment with sufficient confidence. It is located between the minimum I/B ratio of samples in which the genetic segment is known to be present [$p(I/B)_1$] and the maximum I/B ratio of samples in which the genetic segment is known to be absent [$a(I/B)_n$].

The value of $U_{NC}$ is calculated from the measure of central tendency, for example arithmetic mean, other means, median and minimum I/B ratios of samples in which the genetic segment is known to be present [pMedian I/B, $p(I/B)_1$]. Specifically, $U_{NC}$ is such that the distances from $U_{NC}$ to $T_{I/B}$ and $p(I/B)_1$ to $T_{I/B}$ are proportional to the distances from $p(I/B)_1$ to $T_{I/B}$ and pMedian I/B to $T^{I/B}$.

$$\frac{U_{NC} - T_{I/B}}{p(I/B)_1 - T_{I/B}} = \frac{p(I/B)_1 - T_{I/B}}{pMedian\ I/B - T_{I/B}}$$

Therefore, $$U_{NC} = \frac{T_{I/B} \cdot [pMedian\ I/B - 2 \cdot p(I/B)_1] + p(I/B)_1^2}{pMedian\ I/B - T_{I/B}}$$

Second, for each optimal probe set the lower boundary of the "No Call" I/B region ($L_{NC}$) is calculated. The value $L_{NC}$ is calculated from the measure of central tendency, for example arithmetic mean, other means, median and maximum I/B ratios of samples in which the genetic segment is known to be absent [aMedian I/B, $a(I/B)_n$]. Specifically, $L_{NC}$ is such that the distances from $L_{NC}$ to $T_{I/B}$ and $a(I/B)_n$ to $T_{I/B}$ be proportional to the distances from $a(I/B)_n$ to $T_{I/B}$ and aMedian I/B to $T_{I/B}$.

$$\frac{T_{I/B} - L_{NC}}{T_{I/B} - a(I/B)_n} = \frac{T_{I/B} - a(I/B)_n}{T_{I/B} - aMedian\ I/B}$$

Therefore, $$L_{NC} = \frac{T_{I/B} \cdot [2 \cdot a(I/B)_n - aMedian\ I/B] - a(I/B)_n^2}{T_{I/B} - aMedian\ I/B}$$

Determining Presence Versus Absence of a Genetic Segment in a Test Sample

The present invention provides, in certain aspects, a method for establishing the presence versus absence of a genetic segment in a test sample by means of I/B ratios from optimal probe sets.

Determination of the presence versus absence of the genetic segment of interest in a test sample may be performed according to the values of the I/B ratios of one or more optimal probe sets ($PS_1$, $PS_2$, etc.) for that sample and the values of $U_{NC}$, $L_{NC}$.

For example, when only one probe set ($PS_1$) is used, the genetic segment of interest is determined to be present when $PS_1$ I/B>determined to be absent when $PS_1$ I/B<$L_{NC}$, and no call is determined when $U_{NC} \geq PS_1$ I/B$\geq L_{NC}$.

For example, when two or more probe sets are used, determination of the presence or absence of the genetic segment of interest can be made: a) by a strict consensus of either a present call or an absent call for all the probe sets used (Table 1: example for two probe sets); or b) by a majority consensus with no contradictory calls for all the probe sets used (Table 2: example for two probe sets).

TABLE 1 strict consensus

| Value of $PS_1$ I/B | Value of $PS_2$ I/B | Call for genetic |
|---|---|---|
| $PS_1$ I/B > $U_{NC}$ | $PS_2$ I/B > $U_{NC}$ | Present |
| $PS_1$ I/B < $L_{NC}$ | $PS_2$ I/B < $L_{NC}$ | Absent |
| $U_{NC} \geq PS_1$ I/B $\geq L_{NC}$ | $U_{NC} \geq PS_2$ I/B $\geq L_{NC}$ | No Call |
| $U_{NC} \geq PS_1$ I/B $\geq L_{NC}$ | $PS_2$ I/B > $U_{NC}$ | No Call |
| $U_{NC} \geq PS_1$ I/B $\geq L_{NC}$ | $PS_2$ I/B < $L_{NC}$ | No Call |
| $PS_1$ I/B > $U_{NC}$ | $U_{NC} \geq PS_2$ I/B $\geq L_{NC}$ | No Call |
| $PS_1$ I/B < $L_{NC}$ | $U_{NC} \geq PS_2$ I/B $\geq L_{NC}$ | No Call |

Table 1 shows the determination of the presence or absence of the genetic segment of interest in a sample by a strict consensus of either a present call or an absent call when two probe sets are used.

TABLE 2 majority consensus

| Value of $PS_1$ I/B | Value of $PS_2$ I/B | Call for genetic |
|---|---|---|
| $PS_1$ I/B > $U_{NC}$ | $PS_2$ I/B > $U_{NC}$ | Present |
| $PS_1$ I/B < $L_{NC}$ | $PS_2$ I/B < $L_{NC}$ | Absent |
| $U_{NC} \geq PS_1$ I/B $\geq L_{NC}$ | $U_{NC} \geq PS_2$ I/B $\geq L_{NC}$ | No Call |
| $U_{NC} \geq PS_1$ I/B $\geq L_{NC}$ | $PS_2$ I/B > $U_{NC}$ | Present |
| $U_{NC} \geq PS_1$ I/B $\geq L_{NC}$ | $PS_2$ I/B < $L_{NC}$ | Absent |
| $PS_1$ I/B > $U_{NC}$ | $U_{NC} \geq PS_2$ I/B $\geq L_{NC}$ | Present |
| $PS_1$ I/B < $L_{NC}$ | $U_{NC} \geq PS_2$ I/B $\geq L_{NC}$ | Absent |

Table 2 shows the determination of the presence or absence of the genetic segment of interest in a sample by a majority consensus with no contradictory calls of either a present call or an absent call when two probe sets are used.

The following is presented by way of example and is not to be construed as a limitation to the scope of the claims.

EXAMPLE

RHD Gene Exon 5 Determination

The following example relates to a method of genotyping of human blood groups, such as Rhesus (RH). The method described herein has been applied to 11 probe sets in Blood Group Genotyping that interrogate RHD exon 05 variants (SNPs). The process described below proceeds from the analysis of two sets of samples, one consisting of 197 samples where RHD exon 05 is known to be present, the other consisting of 161 samples where RHD exon 05 is known to be absent.

Materials and Methods

According to the present example, samples containing nucleic acid were taken from blood. DNA extraction was carried out in accordance with the protocol provided by the manufacturer for purification of Genomic DNA ("QIAamp® DNA Blood Mini or Midi Kit"). Purified DNA was quantified in a measuring apparatus (spectrophotometer) to check concentration and A260/A280 ratio (1.6-1.95).

DNA regions which may contain the genetic segments whose presence or absence is to be determined were subjected to an amplification reaction in order to obtain amplification products. Any suitable technique or method may be used for amplification. Multiplex PCR were carried out, using appropriate pairs of oligonucleotide PCR primers. 38 cycles of 3 steps (denaturalization for 45 s at 95° C., annealing for 60 s at 60° C., and extension for 90 s at 72° C.) were followed by a final extension at 72° C. for 10 min.

PCR products were then fragmented using a fragmentation mix containing 0.32 mM EDTA, 0.18 U/µl alkaline phosphatase and 04 U/µl DNAse I, by incubation at 37° C. for 30 minutes, followed by heat inactivation at 95° C. for 10 minutes.

Fragmentation products then underwent indirect labelling with Biotin-11-ddUTP using standard techniques by incubation at 37° C. for 60 minutes.

Labelled fragmentation products were then contacted with oligonucleotide probes, which are capable of detecting the corresponding genetic segments by hybridisation under suitable conditions, fixed on a solid support. Typically the hybridisation conditions allow specific hybridisation between probes and corresponding target nucleic acids to form specific probe/target hybridisation complexes while minimising hybridisation between probes carrying one or more mismatches to the DNA. Hybridisation took place at room temperature, under 40 psi (2.7 bar) of $N_2$ pressure, for 90 minutes. Probe sets used were as shown in Table 3 below:

TABLE 3

| PROBE SET NUMBER | PROBE SEQUENCE | SEQ ID NO: |
|---|---|---|
| 1 | AGAAGTCCAATCGAAAGGAAGAATG | 102 |
| 1 | AGAAGTCCAATCTAAAGGAAGAATG | 103 |
| 1 | GAAGTCCAATCGAAAGGAAGAAT | 104 |
| 1 | GAAGTCCAATCTAAAGGAAGAAT | 105 |
| 2 | CAAGGACTATCAGGCCACGGGGTCA | 106 |
| 2 | CAAGGACTATCAGCCCACGGGGTCA | 107 |
| 2 | TGACCCCGTGGCCTGATAGTCCTTG | 108 |
| 2 | TGACCCCGTGGGCTGATAGTCCTTG | 109 |
| 3 | CTGGCCCCCAGGCGCCCTCTTCT | 110 |
| 3 | CTGGCCCCCAGTCGCCCTCTTCT | 111 |
| 3 | CTGGCCCCCAGGCGCCCTCTTCT | 110 |
| 3 | CTGGCCCCCAGTCGCCCTCTTCT | 111 |
| 4 | CTGGCCAAGTTTCAACTCTGC | 112 |
| 4 | CTGGCCAAGTGTCAACTCTGC | 113 |
| 4 | TGGCCAAGTTTCAACTCTG | 114 |
| 4 | TGGCCAAGTGTCAACTCTG | 115 |

TABLE 3-continued

| PROBE SET NUMBER | PROBE SEQUENCE | SEQ ID NO: |
|---|---|---|
| 5 | AGTTTCAACTCTGCTCTGCTGAGAA | 116 |
| 5 | AGTTTCAACTCTCCTCTGCTGAGAA | 117 |
| 5 | AGTTTCAACTCTGCTCTGCTGAGAA | 116 |
| 5 | AGTTTCAACTCTCCTCTGCTGAGAA | 117 |
| 6 | CTGCTCTGCTGAGAAGTCCAATCGA | 118 |
| 6 | CTGCTCTGCTGAAAAGTCCAATCGA | 119 |
| 6 | TGCTCTGCTGAGAAGTCCAATCG | 120 |
| 6 | TGCTCTGCTGAAAAGTCCAATCG | 121 |
| 7 | AGAAGTCCAATCGAAAGGAAGAATG | 102 |
| 7 | AGAAGTCCAATCCAAAGGAAGAATG | 122 |
| 7 | GAAGTCCAATCGAAAGGAAGAAT | 104 |
| 7 | GAAGTCCAATCCAAAGGAAGAAT | 123 |
| 8 | AGGAAGAATGCCGTGTTCAACAC | 26 |
| 8 | AGGAAGAATGCCGTGTTCAACACC | 27 |
| 8 | AGGAAGAATGCCGTGTTCAACAC | 26 |
| 8 | AGGAAGAATGCCGTGTTCAACACC | 27 |
| 9 | GGAAGAATGCCGTGTTCAACACC | 124 |
| 9 | GGAAGAATGCCATGTTCAACACC | 125 |
| 9 | GAAGAATGCCGTGTTCAACAC | 126 |
| 9 | GAAGAATGCCATGTTCAACAC | 127 |
| 10 | GGCTCACCCCCAAGGGAAGGGAAGA | 28 |
| 10 | GGCTCACCCCCAGGGAAGGGAAGAT | 29 |
| 10 | GGCTCACCCCCAAGGGAAGGGAAGA | 28 |
| 10 | GGCTCACCCCCAGGGAAGGGAAGAT | 29 |
| 11 | AGAAGTCCAATCGAAAGGAAGAATG | 102 |
| 11 | AGAAGTCCAATCAAAAGGAAGAATG | 128 |
| 11 | GAAGTCCAATCGAAAGGAAGAAT | 104 |
| 11 | GAAGTCCAATCAAAAGGAAGAAT | 129 |

After hybridisation, a streptavidine-Cy3 conjugate was added to complete the indirect labelling. Fluorescence signal detection and quantification was performed using a Innopsys® 700A/710 scanner.

Results and Discussion

The following distribution of I/B ratios was derived for each of the 11 probe sets (PS1-PS11) in a sample set of size m=197 in which RHD exon05 is known to be present (p).

$$p(I/B)_1 < p(I/B)_2 < \ldots < p(I/B)_{m-1} < p(I/B)_m$$

$p_{PS1}$: 2.4; 3.1; 3.2; 3.5; 3.8; 3.8; 4.0; 4.0; 4.0; 4.1; 4.1; 4.1; 4.1; 4.2; 4.2; 4.2; 4.2; 4.3; 4.3; 4.3; 4.3; 4.3; 4.4; 4.4; 4.4; 4.4; 4.4; 4.5; 4.5; 4.5; 4.5; 4.5; 4.5; 4.5; 4.6; 4.6; 4.6; 4.6; 4.6; 4.6; 4.6; 4.6; 4.7; 4.7; 4.7; 4.7; 4.7; 4.7; 4.7; 4.8; 4.8; 4.8; 4.9; 4.9; 4.9; 4.9; 4.9; 4.9; 4.9; 4.9; 4.9; 5.0; 5.0; 5.0; 5.0; 5.0; 5.0; 5.0; 5.0; 5.0; 5.0; 5.0; 5.0; 5.1; 5.1; 5.1; 5.1; 5.1; 5.1; 5.2; 5.2; 5.2; 5.2; 5.2; 5.2; 5.3; 5.3; 5.3; 5.3; 5.3; 5.3; 5.4; 5.4; 5.4; 5.4; 5.4; 5.4; 5.4; 5.5; 5.5; 5.5; 5.6; 5.6; 5.6; 5.6; 5.7; 5.8; 5.9; 5.9; 5.9; 5.9; 5.9; 5.9; 5.9; 6.0; 6.0; 6.1; 6.1; 6.1; 6.1; 6.1; 6.2; 6.3; 6.3; 6.3; 6.3; 6.3; 6.5; 6.5; 6.6; 6.6; 6.7; 6.8; 6.9; 6.9; 7.0; 7.1; 7.1; 7.2; 7.2; 7.3; 7.4; 7.5; 7.5; 7.5; 7.6; 7.6; 7.6; 7.6; 7.6; 7.6; 7.6; 7.6; 7.7; 7.7; 7.8; 7.9; 8.2; 8.2; 8.3; 8.4; 8.5; 8.5; 8.5; 8.8; 8.8; 8.8; 8.8; 8.9; 9.0; 9.0; 9.1; 9.2; 9.3; 9.3; 9.4; 9.5; 9.5; 9.5; 9.5; 9.6; 9.6; 9.8; 9.8; 9.8; 9.9; 10.1; 10.2; 10.3; 10.4; 10.4; 11.1; 12.8; 12.9; 19.9

$p_{PS2}$: 23.0; 23.1; 26.5; 28.2; 29.1; 30.5; 30.9; 32.1; 32.6; 33.1; 33.2; 34.2; 34.4; 35.2; 35.6; 36.0; 36.5; 37.7; 38.0; 38.1; 38.3; 39.3; 39.9; 40.0; 40.2; 40.3; 40.3; 40.4; 40.8; 41.1; 41.8; 42.2; 42.7; 43.0; 43.5; 43.7; 44.5; 45.0; 45.4; 45.7; 46.1; 46.6; 46.8; 46.8; 47.0; 48.0; 49.5; 50.7; 51.5; 51.6; 51.7; 51.7; 51.7; 52.0; 52.1; 53.0; 53.0; 53.1; 53.1; 53.2; 53.2; 53.5; 53.7; 53.8; 54.5; 55.2; 55.6; 55.8; 56.9; 57.2; 57.4; 57.7; 57.7; 58.3; 58.4; 58.9; 59.4; 59.8; 59.9; 59.9; 59.9; 60.0; 60.2; 60.7; 60.8; 61.0; 61.1; 61.5; 61.7; 62.7; 62.8; 62.9; 63.3; 63.4; 63.6; 63.6; 64.2; 65.0; 65.3; 65.5; 65.9; 67.0; 67.3; 67.5; 67.6; 67.6; 68.9; 70.8; 71.4; 71.9; 72.1; 72.4; 72.7; 73.0; 73.2; 73.6; 73.8; 74.7; 75.8; 76.6; 77.1; 77.1; 78.4; 78.6; 79.1; 79.1; 80.3; 81.3; 81.3; 82.4; 83.4; 84.2; 86.4; 86.6; 87.6; 87.7; 88.4; 89.5; 89.5; 90.9; 91.4; 91.9; 92.9; 94.1; 94.4; 97.2; 97.4; 98.2; 98.6; 98.8; 99.0; 99.1; 99.5; 100.2; 101.2; 102.0; 102.1; 102.5; 102.6; 102.7; 104.0; 104.1; 104.5; 104.6; 105.7; 106.0; 106.1; 106.1; 107.3; 107.3; 107.9; 108.0; 108.1; 109.5; 110.1; 110.5; 112.6; 113.2; 113.8; 114.6; 116.4; 117.2; 120.0; 121.2; 122.1; 124.8; 127.5; 127.9; 128.8; 129.6; 129.7; 133.1; 133.9; 135.4; 135.5; 139.8; 147.7

$p_{PS3}$: 10.2; 10.4; 11.0; 12.3; 12.7; 13.0; 13.2; 13.3; 13.3; 13.6; 14.3; 14.9; 14.9; 15.0; 15.4; 15.6; 15.7; 15.8; 16.0; 16.5; 16.6; 16.6; 16.8; 16.9; 17.0; 17.1; 17.1; 17.3; 17.4; 17.4; 18.0; 18.2; 18.3; 18.4; 18.5; 19.0; 19.3; 19.3; 19.3; 19.5; 19.6; 19.9; 20.1; 20.1; 20.1; 20.4; 20.5; 20.5; 20.7; 20.8; 20.9; 20.9; 21.1; 21.5; 21.6; 21.9; 21.9; 21.9; 21.9; 22.1; 22.3; 22.3; 22.4; 22.6; 22.6; 22.8; 22.9; 22.9; 23.1; 23.1; 23.2; 23.2; 23.3; 23.4; 23.9; 24.0; 24.1; 24.3; 24.3; 24.3; 24.4; 24.4; 24.6; 24.7; 24.9; 24.9; 25.2; 25.3; 25.4; 25.4; 25.8; 25.8; 26.0; 26.1; 26.3; 26.4; 26.5; 26.6; 26.7; 26.8; 27.4; 27.7; 27.7; 27.8; 27.9; 27.9; 28.0; 28.3; 28.4; 28.8; 28.9; 28.9; 28.9; 29.1; 29.5; 29.5; 29.5; 29.9; 30.1; 30.1; 30.4; 30.4; 30.7; 30.8; 31.5; 31.8; 32.0; 32.0; 32.2; 32.3; 32.4; 33.8; 34.1; 34.2; 34.8; 35.1; 35.5; 35.6; 35.6; 36.5; 36.9; 36.9; 38.0; 38.0; 39.3; 39.8; 40.4; 40.4; 40.5; 40.7; 40.9; 41.0; 41.3; 41.9; 42.3; 42.6; 42.7; 42.7; 42.8; 42.8; 42.8; 43.3; 43.4; 43.4; 43.5; 43.5; 43.5; 43.9; 44.0; 44.1; 44.8; 45.0; 45.1; 46.7; 46.7; 46.8; 47.1; 47.3; 47.4; 48.0; 48.2; 49.3; 49.4; 49.9; 49.9; 50.2; 51.2; 51.8; 53.0; 53.2; 53.3; 53.5; 54.4; 55.7; 57.4; 57.9; 62.8

$p_{PS4}$: 22.1; 22.2; 22.6; 27.0; 27.5; 27.8; 29.1; 29.2; 29.7; 30.1; 30.6; 31.6; 32.0; 32.2; 32.3; 32.8; 33.0; 34.4; 34.5; 34.5; 35.7; 37.9; 38.1; 38.3; 38.5; 38.5; 38.6; 38.8; 38.9; 38.9; 39.1; 39.1; 39.2; 39.4; 40.1; 40.4; 40.8; 40.9; 40.9; 41.2; 41.4; 41.6; 42.0; 42.2; 42.3; 42.3; 42.5; 42.8; 43.1; 43.2; 43.6; 43.9; 44.9; 45.1; 45.3; 45.5; 45.9; 45.9; 46.0; 46.1; 46.2; 47.6; 47.6; 47.6; 47.7; 47.7; 47.8; 48.1; 48.1; 48.4; 48.5; 48.8; 48.9; 49.2; 49.4; 50.1; 50.4; 50.6; 51.0; 51.4; 51.5; 51.8; 51.8; 51.9; 52.5; 52.6; 52.8; 53.0; 53.2; 53.5; 54.3; 54.3; 54.6; 54.7; 54.7; 54.7; 55.3; 55.9; 56.1; 56.3; 56.5; 56.6; 56.9; 57.7; 57.8; 58.0; 59.2; 59.5; 60.1; 61.0; 61.4; 61.6; 62.2; 62.3; 62.5; 62.6; 63.3; 64.1; 65.6; 66.1; 66.5; 68.0; 68.5; 69.7; 70.6; 72.1; 72.2; 73.7; 74.7; 75.5; 75.7; 76.2; 77.4; 78.2; 80.6; 80.8; 82.6; 84.0; 86.4; 87.3; 88.4; 91.4; 91.6; 92.3; 93.3; 93.4; 95.4; 95.9; 96.1; 96.4; 96.7; 98.0; 98.5; 98.5; 98.6; 99.5; 99.7; 99.7;

100.1; 100.1; 100.3; 100.5; 100.6; 101.4; 102.3; 103.5; 103.5; 104.7; 105.1; 105.6; 105.6; 106.3; 106.7; 109.7; 111.0; 111.1; 112.5; 112.9; 113.3; 113.6; 114.1; 115.9; 119.1; 119.5; 120.3; 121.5; 121.7; 128.0; 129.5; 131.4; 136.7; 139.9; 151.5; 157.7; 159.0; 161.8; 163.6

$p_{PS5}$: 18.6; 19.2; 19.5; 22.3; 23.6; 23.6; 24.7; 27.0; 27.1; 28.3; 28.7; 28.7; 29.0; 29.1; 29.4; 29.7; 30.0; 30.8; 30.8; 30.8; 31.8; 32.0; 32.3; 32.3; 32.6; 33.1; 33.9; 34.1; 34.2; 34.6; 34.6; 34.8; 34.9; 35.1; 35.3; 35.6; 35.9; 36.2; 36.3; 36.5; 36.8; 37.1; 37.7; 37.7; 37.7; 38.1; 38.2; 38.6; 38.9; 39.0; 39.1; 39.3; 39.4; 39.5; 39.6; 40.3; 40.4; 40.4; 40.5; 40.5; 40.7; 40.7; 40.9; 41.0; 41.3; 41.8; 42.0; 42.0; 42.7; 42.7; 43.0; 43.4; 43.4; 43.6; 43.8; 43.8; 43.9; 44.1; 44.5; 44.6; 44.6; 44.6; 44.6; 44.7; 44.8; 45.6; 46.3; 47.0; 47.0; 47.1; 47.1; 47.3; 47.5; 47.9; 48.1; 48.2; 48.3; 48.4; 48.8; 49.2; 49.6; 49.9; 50.3; 50.5; 50.6; 50.6; 50.7; 51.0; 51.6; 51.8; 52.1; 52.8; 52.8; 53.0; 54.3; 54.6; 55.6; 56.1; 56.5; 56.8; 56.9; 57.4; 58.1; 58.2; 58.6; 59.0; 59.2; 59.5; 59.6; 59.7; 61.3; 61.9; 64.2; 64.4; 64.9; 65.1; 66.0; 66.9; 67.3; 68.5; 68.8; 70.4; 70.6; 70.8; 71.5; 71.9; 72.2; 72.5; 72.8; 72.8; 74.0; 74.2; 74.4; 74.6; 74.6; 76.1; 76.4; 77.4; 77.7; 78.0; 78.1; 78.4; 79.6; 79.8; 80.0; 80.2; 80.2; 80.4; 80.8; 80.9; 81.9; 81.9; 82.1; 82.2; 82.4; 83.0; 83.2; 83.9; 84.7; 85.3; 85.8; 85.9; 86.5; 87.0; 87.7; 88.1; 88.2; 90.4; 90.5; 93.9; 94.2; 95.1; 97.1; 98.4; 101.3; 110.5; 137.5

$p_{PS6}$: 8.9; 9.8; 10.5; 10.7; 11.2; 13.2; 13.3; 13.4; 13.5; 13.5; 13.6; 13.6; 13.6; 13.8; 13.9; 14.2; 14.3; 14.4; 14.4; 14.6; 15.0; 15.0; 15.2; 15.2; 15.2; 15.4; 15.4; 15.7; 15.7; 16.0; 16.0; 16.2; 16.4; 16.7; 16.8; 16.9; 17.0; 17.0; 17.2; 17.2; 17.4; 17.4; 17.4; 17.6; 17.6; 17.7; 17.9; 17.9; 18.0; 18.0; 18.0; 18.0; 18.0; 18.1; 18.3; 18.3; 18.4; 18.5; 18.6; 18.7; 19.0; 19.0; 19.0; 19.2; 19.3; 19.3; 19.3; 19.4; 19.5; 19.6; 19.8; 19.8; 19.9; 20.0; 20.0; 20.3; 20.3; 20.3; 20.4; 20.5; 20.5; 20.5; 20.5; 20.7; 20.9; 20.9; 20.9; 21.0; 21.0; 21.0; 21.1; 21.1; 21.1; 21.2; 21.3; 21.4; 21.7; 21.9; 21.9; 21.9; 21.9; 22.0; 22.4; 22.4; 22.9; 22.9; 23.0; 23.2; 23.4; 23.5; 23.8; 23.8; 24.1; 24.1; 24.1; 24.4; 24.8; 25.0; 25.3; 25.5; 25.9; 25.9; 26.0; 27.0; 27.4; 27.6; 28.2; 28.3; 29.0; 29.4; 30.5; 30.7; 30.9; 31.2; 31.3; 31.5; 31.9; 31.9; 32.1; 32.1; 32.4; 32.6; 32.6; 32.8; 33.1; 33.3; 33.4; 33.9; 34.4; 34.8; 35.0; 35.0; 35.3; 35.3; 35.4; 35.6; 35.6; 35.8; 35.9; 36.0; 36.1; 36.2; 36.3; 36.4; 36.6; 36.8; 36.9; 37.0; 37.1; 37.1; 37.4; 37.6; 38.0; 38.1; 38.3; 38.6; 39.2; 39.6; 40.1; 40.4; 40.5; 40.5; 40.8; 41.3; 42.1; 42.1; 42.3; 42.7; 43.2; 44.4; 45.8; 45.9; 45.9; 47.6; 54.9; 57.3; 58.1

$p_{PS7}$: 9.6; 9.7; 10.2; 11.3; 11.6; 12.2; 12.6; 12.6; 12.7; 12.9; 13.3; 13.3; 13.7; 14.0; 14.1; 14.2; 14.2; 14.3; 14.5; 14.5; 14.6; 14.8; 14.9; 14.9; 15.1; 15.4; 15.4; 15.5; 15.5; 16.1; 16.2; 16.2; 16.3; 16.4; 16.4; 16.5; 16.8; 16.9; 17.1; 17.1; 17.1; 17.2; 17.3; 17.5; 17.5; 17.5; 17.6; 17.7; 17.7; 17.8; 17.8; 17.9; 18.0; 18.0; 18.0; 18.3; 18.3; 18.4; 18.4; 18.4; 18.5; 18.5; 18.6; 18.7; 18.7; 19.0; 19.0; 19.1; 19.2; 19.3; 19.5; 19.6; 19.6; 19.7; 19.7; 19.9; 19.9; 20.0; 20.1; 20.1; 20.1; 20.3; 20.3; 20.4; 20.5; 20.6; 20.8; 20.9; 20.9; 21.1; 21.1; 21.2; 21.5; 21.6; 21.7; 21.9; 22.1; 22.4; 22.4; 22.5; 22.5; 22.5; 22.5; 22.7; 22.9; 23.1; 23.1; 23.1; 23.5; 23.7; 23.7; 23.7; 23.7; 23.9; 24.2; 24.2; 24.6; 24.6; 25.3; 25.5; 25.6; 26.1; 26.4; 26.8; 28.4; 29.6; 29.7; 30.1; 30.1; 30.7; 30.8; 31.1; 31.4; 31.4; 31.6; 32.1; 32.4; 32.6; 32.7; 33.0; 33.0; 33.2; 33.5; 33.5; 33.9; 34.1; 34.3; 34.6; 34.7; 34.7; 34.7; 34.7; 34.8; 35.3; 35.4; 35.7; 35.8; 36.0; 36.0; 36.0; 36.0; 36.1; 36.2; 36.4; 36.6; 36.8; 36.8; 37.4; 37.6; 38.1; 38.2; 38.4; 39.0; 39.1; 39.4; 40.1; 40.2; 40.4; 40.5; 40.8; 41.3; 41.3; 41.6; 42.3; 42.6; 43.1; 43.5; 43.5; 44.1; 45.1; 46.6; 49.8; 50.3; 51.3; 56.4; 57.1; 59.6

$p_{PS8}$: 9.7; 10.1; 11.2; 12.2; 12.6; 12.9; 13.2; 13.4; 13.5; 13.6; 13.7; 13.7; 14.1; 14.1; 14.2; 14.4; 14.5; 14.5; 14.6; 14.8; 14.9; 15.0; 15.1; 15.3; 15.3; 15.3; 15.5; 15.7; 15.8; 16.1; 16.2; 16.2; 16.5; 16.9; 17.0; 17.0; 17.1; 17.2; 17.3; 17.6; 17.6; 17.8; 17.8; 17.8; 17.9; 18.0; 18.0; 18.2; 18.2; 18.4; 18.5; 18.6; 18.8; 19.1; 19.3; 19.3; 19.3; 19.4; 19.4; 19.5; 19.7; 19.7; 19.8; 20.1; 20.2; 20.3; 20.3; 20.4; 20.4; 20.4; 20.7; 20.8; 20.9; 20.9; 21.0; 21.1; 21.1; 21.1; 21.2; 21.2; 21.2; 21.3; 21.4; 21.4; 21.5; 21.7; 21.9; 22.0; 22.0; 22.2; 22.2; 22.2; 22.5; 22.5; 22.8; 22.9; 23.0; 23.1; 23.2; 23.3; 23.6; 23.7; 23.7; 23.8; 23.8; 24.0; 24.1; 24.3; 24.3; 24.4; 24.8; 25.0; 25.2; 25.5; 25.9; 25.9; 26.0; 26.1; 26.3; 26.4; 26.8; 26.8; 27.6; 27.7; 28.1; 28.6; 29.8; 29.8; 30.1; 30.4; 30.7; 30.9; 31.8; 31.8; 31.9; 32.1; 32.3; 32.8; 32.9; 33.0; 33.4; 33.4; 33.5; 33.5; 33.6; 34.0; 34.3; 34.5; 34.6; 34.6; 34.9; 35.0; 35.4; 35.5; 35.7; 35.8; 35.8; 36.1; 36.2; 36.2; 36.2; 36.4; 36.5; 36.8; 37.4; 37.4; 37.4; 37.6; 38.0; 38.1; 38.1; 38.1; 38.2; 38.2; 38.6; 38.7; 39.0; 39.3; 39.5; 39.9; 40.2; 40.3; 40.4; 40.6; 41.0; 41.2; 42.3; 42.5; 44.6; 44.7; 46.4; 48.4; 49.8; 51.0; 51.2; 53.3

$p_{PS9}$: 20.7; 21.1; 22.9; 23.4; 23.8; 25.2; 26.1; 27.1; 27.2; 27.5; 28.8; 28.9; 29.5; 29.7; 29.7; 30.1; 30.3; 30.4; 30.6; 30.6; 30.9; 30.9; 31.0; 31.3; 31.6; 31.6; 31.7; 31.8; 31.8; 32.3; 32.4; 32.5; 33.0; 33.2; 33.8; 34.5; 35.1; 35.1; 35.6; 35.6; 36.1; 36.2; 36.2; 36.7; 36.7; 36.8; 37.1; 37.1; 37.1; 38.1; 38.4; 38.5; 38.6; 38.9; 39.1; 39.3; 39.5; 39.6; 39.6; 39.7; 39.9; 39.9; 39.9; 40.0; 40.0; 40.3; 40.4; 40.8; 40.9; 41.0; 41.2; 41.5; 41.5; 41.6; 41.8; 42.0; 42.0; 42.4; 42.5; 42.9; 42.9; 42.9; 42.9; 43.0; 43.1; 43.2; 43.2; 43.3; 43.6; 43.6; 43.8; 44.0; 44.1; 44.2; 44.4; 45.4; 45.6; 45.7; 45.7; 45.8; 46.2; 46.4; 46.8; 46.9; 47.4; 47.5; 47.7; 47.9; 47.9; 48.5; 48.6; 48.8; 48.9; 48.9; 49.2; 49.4; 50.4; 50.7; 50.8; 51.0; 51.3; 51.6; 52.9; 53.3; 53.4; 53.5; 53.8; 54.1; 54.2; 55.2; 55.7; 56.5; 57.0; 57.5; 58.7; 59.0; 59.4; 59.6; 60.6; 61.5; 61.6; 61.8; 62.6; 62.9; 63.0; 63.3; 63.5; 64.0; 64.2; 64.6; 64.9; 65.1; 65.3; 65.3; 65.3; 65.7; 65.7; 65.8; 65.8; 66.4; 67.7; 67.7; 67.8; 67.8; 68.5; 69.8; 69.9; 69.9; 70.2; 71.3; 71.4; 71.7; 73.0; 73.0; 73.3; 73.5; 73.5; 73.9; 74.9; 74.9; 75.8; 75.8; 75.8; 76.6; 76.6; 76.8; 77.7; 78.4; 78.9; 80.2; 86.0; 91.1; 91.3; 94.5; 96.2; 99.8; 108.6

$p_{PS10}$: 17.7; 16.4; 16.9; 18.6; 20.3; 21.0; 21.2; 21.8; 21.9; 22.5; 22.5; 22.5; 22.6; 23.3; 23.3; 23.9; 24.1; 24.5; 24.6; 24.8; 25.0; 25.4; 25.4; 25.5; 25.5; 25.6; 25.8; 26.2; 26.4; 26.5; 26.8; 26.8; 27.7; 27.8; 28.0; 28.0; 28.2; 28.3; 28.6; 28.7; 29.4; 29.6; 29.6; 29.7; 29.8; 29.9; 30.0; 30.0; 30.2; 30.3; 30.3; 30.3; 30.4; 30.7; 30.9; 30.9; 31.0; 31.0; 31.1; 31.4; 31.5; 31.6; 31.7; 31.9; 32.1; 32.3; 32.4; 32.6; 32.6; 32.8; 32.9; 32.9; 33.1; 33.2; 33.3; 33.4; 33.6; 33.6; 33.7; 34.0; 34.0; 34.2; 34.3; 34.5; 34.7; 34.9; 35.0; 35.1; 35.2; 35.4; 35.5; 35.8; 35.8; 35.9; 36.2; 36.7; 37.1; 37.3; 37.4; 37.4; 37.5; 37.5; 37.7; 38.2; 38.3; 38.3; 38.4; 38.4; 38.8; 38.9; 39.1; 39.2; 39.4; 39.6; 39.7; 39.7; 39.9; 40.1; 40.4; 40.8; 40.8; 41.1; 41.7; 42.3; 43.7; 43.9; 43.9; 44.2; 44.4; 44.6; 45.0; 45.6; 45.7; 46.0; 46.2; 47.2; 47.2; 47.8; 47.8; 47.9; 47.9; 48.0; 48.3; 48.3; 48.5; 48.6; 48.7; 49.0; 49.0; 49.7; 49.9; 50.0; 50.2; 50.8; 50.9; 51.1; 51.3; 51.7; 52.6; 52.9; 53.0; 53.1; 53.2; 53.7; 53.8; 54.1; 54.3; 54.4; 54.6; 55.0; 55.1; 55.1; 55.7; 55.8; 56.2; 56.7; 56.8; 56.9; 57.3; 58.2; 58.7; 59.0; 59.3; 59.7; 60.1; 62.3; 62.3; 63.1; 63.7; 64.9; 65.2; 67.6; 72.8; 76.1; 77.0; 77.7; 80.0

$p_{PS11}$: 21.0; 17.4; 17.8; 18.0; 18.5; 18.9; 19.3; 20.2; 20.3; 21.0; 21.2; 21.3; 21.6; 22.0; 22.0; 22.6; 22.7; 22.8; 23.0; 23.1; 23.3; 23.5; 23.5; 23.5; 23.6; 23.7; 23.7; 23.8; 24.0; 24.0; 24.0; 24.1; 24.4; 24.7; 24.7; 24.9; 24.9; 25.2; 25.2; 25.7; 25.7; 25.8; 25.8; 25.8; 26.6; 26.6; 26.7; 26.7; 27.4; 27.6; 27.7; 27.8; 27.8; 27.9; 28.1; 28.1; 28.4; 28.5; 28.6; 28.7; 28.7; 29.2; 29.5; 29.6; 29.7; 29.9; 29.9; 30.2; 30.3; 30.8; 30.9; 30.9; 31.1; 31.2; 31.4; 31.5; 31.7; 31.9; 32.1; 32.2; 32.3; 32.4; 32.5; 32.7; 32.8; 33.3; 33.4; 33.9; 34.0; 34.1; 34.2; 34.4; 34.6; 34.7; 34.8; 34.9; 34.9; 35.0; 35.3; 35.6; 35.6; 35.7; 35.7; 36.4; 36.5; 36.7; 36.7;

36.9; 37.1; 37.1; 37.3; 37.4; 37.5; 38.1; 38.2; 38.2; 38.4; 38.7; 38.9; 38.9; 38.9; 39.5; 39.5; 39.8; 39.9; 40.0; 40.1; 40.2; 40.3; 40.3; 40.4; 40.6; 40.8; 41.0; 41.0; 41.9; 43.0; 43.0; 43.1; 43.2; 43.2; 43.7; 43.8; 44.1; 44.3; 44.4; 45.3; 45.4; 45.6; 45.9; 46.0; 46.0; 46.2; 46.5; 46.5; 46.7; 47.1; 47.7; 47.7; 47.8; 47.8; 48.3; 48.6; 49.6; 49.8; 50.3; 50.5; 50.9; 51.3; 51.5; 51.5; 51.7; 51.8; 52.0; 52.1; 52.4; 52.4; 52.6; 52.7; 53.0; 53.6; 54.3; 55.0; 57.8; 58.1; 58.5; 58.7; 65.6; 65.9; 68.5; 68.8; 70.4; 72.6; 78.7; 81.4

The following distribution of I/B ratios was derived for each of the 11 probe sets (PS1-PS11) in a sample set of size n=161 in which RHD exon05 is known to be absent (a).

$a(I/B)_1 < a(I/B)_2 < \ldots < a(I/B)_{n-1} < a(I/B)_n$ $a_{PS1}$: 0.7; 0.7; 0.7; 0.8; 0.9; 0.9; 0.9; 0.9; 0.9; 1.0; 1.0; 1.0; 1.0; 1.0; 1.0; 1.0; 1.0; 1.0; 1.0; 1.0; 1.0; 1.1; 1.1; 1.1; 1.1; 1.1; 1.1; 1.1; 1.1; 1.1; 1.1; 1.1; 1.1; 1.1; 1.1; 1.1; 1.1; 1.1; 1.2; 1.2; 1.2; 1.2; 1.2; 1.2; 1.2; 1.2; 1.2; 1.2; 1.2; 1.2; 1.2; 1.2; 1.2; 1.2; 1.2; 1.2; 1.2; 1.2; 1.3; 1.3; 1.3; 1.3; 1.3; 1.3; 1.3; 1.3; 1.3; 1.3; 1.3; 1.3; 1.3; 1.3; 1.4; 1.4; 1.4; 1.4; 1.4; 1.4; 1.4; 1.4; 1.4; 1.4; 1.4; 1.4; 1.4; 1.4; 1.4; 1.4; 1.5; 1.5; 1.5; 1.5; 1.5; 1.5; 1.5; 1.5; 1.5; 1.5; 1.5; 1.5; 1.5; 1.6; 1.6; 1.6; 1.6; 1.6; 1.6; 1.6; 1.6; 1.6; 1.6; 1.7; 1.7; 1.7; 1.7; 1.7; 1.7; 1.7; 1.8; 1.8; 1.8; 1.8; 1.8; 1.8; 1.8; 1.8; 1.8; 1.9; 1.9; 1.9; 1.9; 1.9; 2.0; 2.0; 2.0; 2.0; 2.0; 2.0; 2.1; 2.1; 2.1; 2.2; 2.2; 2.2; 2.2; 2.2; 2.2; 2.3; 2.4; 2.4; 2.4; 2.6; 2.6; 2.8; 2.9; 3.3; 3.5; 3.5; 4.2; 4.6

$a_{PS2}$: 1.4; 1.5; 1.6; 1.6; 1.7; 1.7; 1.7; 1.7; 1.8; 2.0; 2.0; 2.0; 2.0; 2.0; 2.1; 2.2; 2.2; 2.2; 2.3; 2.4; 2.4; 2.4; 2.4; 2.5; 2.5; 2.6; 2.6; 2.7; 2.7; 2.7; 2.8; 2.8; 2.8; 2.9; 3.0; 3.1; 3.2; 3.3; 3.3; 3.3; 3.3; 3.3; 3.4; 3.4; 3.5; 3.5; 3.5; 3.5; 3.6; 3.7; 3.7; 3.7; 3.7; 3.7; 3.8; 3.8; 3.9; 3.9; 4.1; 4.1; 4.2; 4.2; 4.2; 4.3; 4.3; 4.4; 4.4; 4.5; 4.5; 4.5; 4.6; 4.6; 4.7; 4.7; 4.7; 4.9; 4.9; 4.9; 5.1; 5.2; 5.3; 5.3; 5.4; 5.4; 5.5; 5.5; 5.5; 5.7; 5.8; 5.8; 5.9; 5.9; 6.0; 6.1; 6.1; 6.2; 6.3; 6.3; 6.4; 6.4; 6.9; 6.9; 7.4; 7.5; 7.6; 7.7; 7.7; 7.8; 7.8; 8.0; 8.1; 8.1; 8.3; 8.5; 8.6; 8.7; 8.7; 8.7; 8.8; 9.0; 9.2; 9.3; 9.7; 9.7; 9.8; 9.9; 9.9; 9.9; 10.0; 10.3; 10.3; 10.5; 10.7; 11.0; 11.7; 12.1; 12.1; 12.6; 12.8; 14.1; 14.6; 15.7; 15.8; 16.1; 16.2; 17.7; 19.3; 19.8; 20.0; 20.2; 20.5; 20.7; 21.2; 21.3; 21.9; 22.3; 22.9; 25.9; 27.4; 27.7; 28.1; 33.2

$a_{PS3}$: 0.9; 0.9; 0.9; 0.9; 0.9; 0.9; 0.9; 1.0; 1.0; 1.0; 1.0; 1.0; 1.0; 1.0; 1.1; 1.1; 1.1; 1.1; 1.1; 1.1; 1.1; 1.2; 1.2; 1.2; 1.2; 1.2; 1.2; 1.2; 1.2; 1.2; 1.2; 1.3; 1.3; 1.3; 1.3; 1.3; 1.3; 1.3; 1.3; 1.3; 1.4; 1.4; 1.4; 1.4; 1.4; 1.4; 1.4; 1.5; 1.5; 1.5; 1.5; 1.5; 1.5; 1.5; 1.5; 1.5; 1.5; 1.5; 1.5; 1.6; 1.6; 1.6; 1.6; 1.7; 1.7; 1.7; 1.7; 1.7; 1.7; 1.7; 1.7; 1.7; 1.8; 1.8; 1.8; 1.8; 1.9; 1.9; 1.9; 1.9; 1.9; 1.9; 1.9; 2.0; 2.0; 2.0; 2.0; 2.1; 2.1; 2.1; 2.2; 2.2; 2.2; 2.2; 2.2; 2.2; 2.2; 2.3; 2.3; 2.3; 2.4; 2.4; 2.4; 2.4; 2.5; 2.5; 2.5; 2.6; 2.6; 2.6; 2.6; 2.6; 2.6; 2.7; 2.7; 2.7; 2.7; 2.7; 2.8; 2.8; 2.9; 3.0; 3.1; 3.1; 3.2; 3.3; 3.3; 3.4; 3.4; 3.4; 3.5; 3.8; 3.8; 3.9; 4.0; 4.0; 4.1; 4.1; 4.1; 4.2; 4.3; 4.3; 4.4; 4.4; 4.6; 4.6; 4.7; 4.8; 4.9; 5.0; 5.4; 5.6; 5.6; 5.8; 6.0; 6.3; 6.5; 6.8; 10.2

$a_{PS4}$: 1.3; 1.6; 1.6; 1.6; 1.7; 1.7; 1.8; 1.8; 2.0; 2.0; 2.1; 2.1; 2.1; 2.1; 2.1; 2.1; 2.2; 2.2; 2.2; 2.2; 2.2; 2.3; 2.3; 2.3; 2.4; 2.4; 2.4; 2.4; 2.5; 2.5; 2.5; 2.6; 2.6; 2.6; 2.6; 2.6; 2.7; 2.7; 2.7; 2.8; 2.8; 2.8; 3.0; 3.0; 3.1; 3.1; 3.1; 3.1; 3.2; 3.2; 3.2; 3.2; 3.2; 3.2; 3.2; 3.3; 3.3; 3.3; 3.3; 3.3; 3.3; 3.3; 3.3; 3.4; 3.4; 3.4; 3.4; 3.4; 3.4; 3.4; 3.4; 3.5; 3.5; 3.5; 3.6; 3.6; 3.6; 3.6; 3.6; 3.7; 3.7; 3.7; 3.7; 3.8; 3.8; 3.9; 3.9; 3.9; 3.9; 3.9; 3.9; 4.0; 4.0; 4.0; 4.1; 4.1; 4.1; 4.2; 4.2; 4.2; 4.2; 4.3; 4.4; 4.4; 4.4; 4.4; 4.5; 4.5; 4.5; 4.6; 4.6; 4.6; 4.6; 4.6; 4.8; 4.8; 4.9; 5.1; 5.1; 5.2; 5.3; 5.3; 5.3; 5.3; 5.4; 5.4; 5.5; 5.5; 5.7; 5.8; 6.0; 6.2; 6.2; 6.3; 6.3; 6.3; 6.8; 7.2; 7.3; 7.6; 7.8; 7.9; 8.3; 8.3; 8.4; 8.5; 8.7; 9.0; 9.5; 9.6; 10.1; 10.5; 11.1; 12.5; 13.4; 14.2; 19.4; 20.1; 26.5

$a_{PS5}$: 0.9; 1.0; 1.0; 1.0; 1.1; 1.1; 1.1; 1.1; 1.1; 1.1; 1.1; 1.2; 1.3; 1.3; 1.4; 1.4; 1.4; 1.4; 1.4; 1.4; 1.5; 1.5; 1.5; 1.6; 1.6; 1.6; 1.6; 1.6; 1.6; 1.6; 1.6; 1.6; 1.7; 1.7; 1.7; 1.7; 1.7; 1.8; 1.8; 1.8; 1.8; 1.8; 1.8; 1.9; 1.9; 1.9; 1.9; 1.9; 1.9; 1.9; 1.9; 1.9; 1.9; 2.0; 2.0; 2.0; 2.0; 2.1; 2.1; 2.1; 2.1; 2.2; 2.2; 2.3; 2.3; 2.3; 2.3; 2.3; 2.4; 2.4; 2.4; 2.4; 2.5; 2.5; 2.5; 2.6; 2.6; 2.6; 2.7; 2.7; 2.7; 2.8; 2.8; 2.9; 2.9; 2.9; 3.0; 3.0; 3.0; 3.0; 3.0; 3.0; 3.0; 3.1; 3.1; 3.1; 3.2; 3.3; 3.3; 3.3; 3.4; 3.5; 3.5; 3.6; 3.7; 3.8; 3.8; 3.9; 3.9; 4.0; 4.0; 4.1; 4.1; 4.2; 4.3; 4.4; 4.4; 4.4; 4.5; 4.6; 4.6; 4.7; 4.8; 4.8; 4.9; 5.0; 5.0; 5.1; 5.3; 5.3; 5.4; 5.5; 5.6; 5.6; 5.7; 6.0; 6.2; 6.5; 6.7; 6.8; 6.8; 6.9; 7.0; 7.5; 7.6; 7.8; 8.0; 8.1; 8.2; 8.9; 8.9; 9.5; 10.3; 10.8; 10.8; 11.1; 11.5; 11.6; 16.4

$a_{PS6}$: 0.7; 0.8; 0.8; 0.8; 0.8; 0.9; 0.9; 0.9; 0.9; 0.9; 0.9; 0.9; 0.9; 0.9; 0.9; 0.9; 1.0; 1.0; 1.0; 1.0; 1.0; 1.0; 1.0; 1.0; 1.0; 1.0; 1.0; 1.0; 1.1; 1.1; 1.1; 1.1; 1.1; 1.1; 1.1; 1.1; 1.1; 1.1; 1.1; 1.1; 1.1; 1.1; 1.1; 1.1; 1.1; 1.1; 1.1; 1.1; 1.1; 1.1; 1.1; 1.1; 1.1; 1.2; 1.2; 1.2; 1.2; 1.2; 1.2; 1.2; 1.2; 1.2; 1.2; 1.2; 1.2; 1.2; 1.2; 1.2; 1.2; 1.3; 1.3; 1.3; 1.3; 1.3; 1.3; 1.3; 1.3; 1.3; 1.3; 1.3; 1.3; 1.3; 1.3; 1.3; 1.3; 1.3; 1.3; 1.3; 1.3; 1.4; 1.4; 1.4; 1.4; 1.4; 1.4; 1.4; 1.4; 1.4; 1.4; 1.4; 1.5; 1.5; 1.5; 1.5; 1.5; 1.5; 1.5; 1.5; 1.5; 1.6; 1.6; 1.6; 1.6; 1.6; 1.6; 1.6; 1.7; 1.7; 1.7; 1.7; 1.8; 1.8; 1.8; 1.9; 1.9; 1.9; 1.9; 2.0; 2.0; 2.0; 2.1; 2.1; 2.1; 2.1; 2.1; 2.2; 2.2; 2.2; 2.3; 2.4; 2.4; 2.5; 2.5; 2.6; 2.6; 2.9; 3.0; 3.2; 3.3; 3.3; 3.3; 3.4; 4.5

$a_{PS7}$: 0.9; 0.9; 0.9; 0.9; 0.9; 1.0; 1.0; 1.0; 1.0; 1.0; 1.0; 1.0; 1.0; 1.0; 1.0; 1.0; 1.0; 1.1; 1.1; 1.1; 1.1; 1.1; 1.1; 1.1; 1.1; 1.2; 1.2; 1.2; 1.2; 1.2; 1.2; 1.2; 1.2; 1.2; 1.2; 1.3; 1.3; 1.3; 1.3; 1.3; 1.3; 1.3; 1.3; 1.3; 1.3; 1.3; 1.3; 1.4; 1.4; 1.4; 1.4; 1.4; 1.4; 1.4; 1.4; 1.4; 1.4; 1.5; 1.5; 1.5; 1.5; 1.5; 1.5; 1.5; 1.5; 1.5; 1.5; 1.5; 1.5; 1.6; 1.6; 1.6; 1.6; 1.6; 1.6; 1.7; 1.7; 1.7; 1.7; 1.8; 1.8; 1.8; 1.8; 1.8; 1.8; 1.8; 1.8; 1.9; 1.9; 1.9; 1.9; 1.9; 1.9; 2.0; 2.0; 2.0; 2.1; 2.1; 2.1; 2.1; 2.1; 2.1; 2.2; 2.2; 2.2; 2.2; 2.2; 2.3; 2.3; 2.3; 2.4; 2.4; 2.4; 2.4; 2.5; 2.5; 2.6; 2.7; 2.7; 2.8; 2.8; 2.8; 2.8; 2.9; 2.9; 3.0; 3.0; 3.0; 3.0; 3.0; 3.0; 3.0; 3.1; 3.1; 3.2; 3.2; 3.2; 3.3; 3.4; 3.5; 3.5; 3.5; 3.5; 3.6; 3.8; 3.9; 4.0; 4.3; 5.0; 5.2; 5.9; 5.9; 6.0; 7.7

$a_{PS8}$: 0.7; 0.7; 0.8; 0.8; 0.8; 0.8; 0.8; 0.8; 0.8; 0.9; 0.9; 0.9; 0.9; 0.9; 0.9; 0.9; 0.9; 0.9; 1.0; 1.0; 1.0; 1.0; 1.0; 1.0; 1.0; 1.0; 1.0; 1.0; 1.0; 1.0; 1.0; 1.0; 1.0; 1.0; 1.0; 1.0; 1.0; 1.1; 1.1; 1.1; 1.1; 1.1; 1.1; 1.1; 1.1; 1.1; 1.1; 1.1; 1.1; 1.1; 1.1; 1.1; 1.1; 1.1; 1.1; 1.1; 1.1; 1.1; 1.1; 1.2; 1.2; 1.2; 1.2; 1.2; 1.2; 1.2; 1.2; 1.2; 1.2; 1.2; 1.2; 1.2; 1.2; 1.2; 1.3; 1.3; 1.3; 1.3; 1.3; 1.3; 1.3; 1.3; 1.3; 1.3; 1.3; 1.3; 1.3; 1.3; 1.3; 1.3; 1.3; 1.3; 1.3; 1.3; 1.3; 1.3; 1.4; 1.4; 1.4; 1.4; 1.4; 1.4; 1.4; 1.4; 1.4; 1.5; 1.5; 1.5; 1.5; 1.5; 1.5; 1.5; 1.6; 1.6; 1.6; 1.6; 1.6; 1.6; 1.7; 1.7; 1.7; 1.7; 1.7; 1.7; 1.7; 1.8; 1.8; 1.8; 1.9; 1.9; 2.0; 2.1; 2.1; 2.1; 2.1; 2.2; 2.2; 2.2; 2.2; 2.3; 2.3; 2.4; 2.5; 2.5; 2.6; 2.7; 2.7; 3.1; 3.1; 3.2; 3.4; 4.6

$a_{PS9}$: 0.7; 0.7; 0.8; 0.8; 0.8; 0.8; 0.8; 0.9; 0.9; 0.9; 0.9; 0.9; 0.9; 0.9; 1.0; 1.0; 1.0; 1.0; 1.0; 1.0; 1.0; 1.0; 1.0; 1.0; 1.0; 1.0; 1.1; 1.1; 1.1; 1.1; 1.1; 1.1; 1.1; 1.1; 1.1; 1.1; 1.1; 1.1; 1.1; 1.1; 1.2; 1.2; 1.2; 1.2; 1.2; 1.2; 1.2; 1.2; 1.2; 1.2; 1.2; 1.3; 1.3; 1.3; 1.3; 1.3; 1.3; 1.3; 1.3; 1.3; 1.3; 1.3; 1.3; 1.3; 1.4; 1.4; 1.4; 1.4; 1.4; 1.4; 1.4; 1.4; 1.4; 1.4; 1.5; 1.5; 1.5; 1.5; 1.5; 1.5; 1.5; 1.5; 1.5; 1.5; 1.5; 1.6; 1.6; 1.6; 1.6; 1.6; 1.6; 1.6; 1.6; 1.6; 1.6; 1.6; 1.6; 1.7; 1.7; 1.7; 1.7; 1.8; 1.8; 1.8; 1.8; 1.8; 1.8; 1.8; 1.9; 1.9; 1.9; 1.9; 2.0; 2.0; 2.0; 2.0; 2.1; 2.1; 2.1; 2.1; 2.1; 2.1; 2.1; 2.2; 2.2; 2.3; 2.3; 2.3; 2.4; 2.4; 2.5; 2.5; 2.5; 2.5; 2.5; 2.6; 2.6; 2.7; 2.8; 2.8; 2.8; 2.8; 3.0; 3.3; 3.4; 3.4; 3.5; 3.5; 3.8; 4.2; 4.8; 5.9

$a_{PS10}$: 0.9; 1.0; 1.0; 1.0; 1.0; 1.0; 1.0; 1.0; 1.1; 1.1; 1.1; 1.1; 1.1; 1.1; 1.1; 1.2; 1.2; 1.2; 1.2; 1.2; 1.2; 1.2; 1.3; 1.3; 1.3; 1.3;

1.3; 1.3; 1.3; 1.3; 1.3; 1.4; 1.4; 1.4; 1.4; 1.4; 1.5; 1.5; 1.5; 1.5; 1.5; 1.5; 1.5; 1.6; 1.6; 1.6; 1.6; 1.6; 1.6; 1.6; 1.6; 1.6; 1.6; 1.6; 1.6; 1.6; 1.7; 1.7; 1.7; 1.7; 1.7; 1.7; 1.7; 1.7; 1.7; 1.7; 1.8; 1.8; 1.8; 1.8; 1.8; 1.8; 1.8; 1.9; 1.9; 1.9; 1.9; 1.9; 2.0; 2.0; 2.1; 2.1; 2.1; 2.2; 2.2; 2.2; 2.2; 2.2; 2.2; 2.2; 2.2; 2.3; 2.3; 2.4; 2.4; 2.4; 2.4; 2.5; 2.5; 2.5; 2.5; 2.5; 2.6; 2.6; 2.6; 2.6; 2.6; 2.6; 2.7; 2.7; 2.8; 2.9; 2.9; 2.9; 3.0; 3.1; 3.2; 3.2; 3.2; 3.4; 3.4; 3.5; 3.5; 3.6; 3.6; 3.6; 3.7; 3.7; 3.7; 3.7; 3.8; 3.8; 3.9; 4.1; 4.1; 4.2; 4.3; 4.4; 4.6; 4.7; 4.7; 4.8; 4.8; 4.8; 4.9; 4.9; 4.9; 5.0; 5.1; 5.6; 5.6; 5.6; 6.1; 6.1; 7.4; 7.7; 7.9; 9.2; 13.4

$a_{PS11}$: 0.5; 0.6; 0.6; 0.6; 0.7; 0.7; 0.7; 0.8; 0.8; 0.8; 0.8; 0.8; 0.8; 0.8; 0.8; 0.8; 0.8; 0.8; 0.8; 0.8; 0.8; 0.8; 0.8; 0.9; 0.9; 0.9; 0.9; 0.9; 0.9; 0.9; 0.9; 0.9; 0.9; 0.9; 0.9; 0.9; 0.9; 0.9; 1.0; 1.0; 1.0; 1.0; 1.0; 1.0; 1.0; 1.0; 1.0; 1.0; 1.0; 1.0; 1.0; 1.0; 1.0; 1.0; 1.0; 1.0; 1.0; 1.0; 1.0; 1.1; 1.1; 1.1; 1.1; 1.1; 1.1; 1.1; 1.1; 1.1; 1.1; 1.1; 1.1; 1.1; 1.1; 1.1; 1.1; 1.1; 1.1; 1.1; 1.1; 1.1; 1.1; 1.1; 1.1; 1.1; 1.1; 1.1; 1.1; 1.1; 1.1; 1.1; 1.1; 1.1; 1.1; 1.2; 1.2; 1.2; 1.2; 1.2; 1.2; 1.2; 1.2; 1.2; 1.2; 1.2; 1.2; 1.2; 1.2; 1.2; 1.2; 1.3; 1.3; 1.3; 1.3; 1.3; 1.3; 1.3; 1.3; 1.3; 1.3; 1.4; 1.4; 1.4; 1.4; 1.4; 1.4; 1.4; 1.5; 1.5; 1.5; 1.5; 1.5; 1.5; 1.5; 1.6; 1.6; 1.6; 1.6; 1.7; 1.7; 1.7; 1.7; 1.7; 1.8; 1.8; 1.8; 1.9; 1.9; 2.0; 2.0; 2.0; 2.1; 2.1; 2.1; 2.2; 2.3; 2.5; 3.0; 3.1; 3.4; 4.5

The amplitude of the interval (A) for each probe set was then calculated as follows: the difference between the smallest I/B ratio in the sample set in which RHD exon 05 is known to be present and the largest I/B ratio in the sample set in which RHD exon 05 is known to be absent.

$$A = p(I/B)_1 - a(I/B)_m$$

$$A_{PS1} = 2.4 - 4.6 = -2.2$$

$$A_{PS2} = 23.0 - 33.2 = -10.3$$

$$A_{PS3} = 10.2 - 10.2 = 0.0$$

$$A_{PS4} = 22.1 - 26.5 = -4.4$$

$$A_{PS5} = 18.6 - 16.4 = 2.1$$

$$A_{PS6} = 8.9 - 4.5 = 4.5$$

$$A_{PS7} = 9.6 - 7.7 = 1.9$$

$$A_{PS8} = 9.7 - 4.6 = 5.2$$

$$A_{PS9} = 20.7 - 5.9 = 14.8$$

$$A_{PS10} = 16.4 - 13.4 = 3.0$$

$$A_{PS11} = 17.4 - 4.5 = 12.9$$

A measure of central tendency, for example arithmetic mean, other means or median is then determined for the I/B ratio for each probe set in the sample set in which RHD exon 05 is known to be present. In this case the measure of central tendency was the median (pMedian I/B).

$$p\mathrm{Median}I/B = \mathrm{Median}\ [p(I/B)_1, \ldots, p(I/B)_n]$$

$$p(\mathrm{Median}I/B)_{PS1} = 5.4$$

$$p(\mathrm{Median}I/B)_{PS2} = 65.3$$

$$p(\mathrm{Median}I/B)_{PS3} = 26.7$$

$$p(\mathrm{Median}I/B)_{PS4} = 56.1$$

$$p(\mathrm{Median}I/B)_{PS5} = 48.8$$

$$p(\mathrm{Median}I/B)_{PS6} = 21.9$$

$$p(\mathrm{Median}I/B)_{PS7} = 22.4$$

$$p(\mathrm{Median}I/B)_{PS8} = 23.1$$

$$p(\mathrm{Median}I/B)_{PS9} = 45.7$$

$$p(\mathrm{Median}I/B)_{PS10} = 37.4$$

$$p(\mathrm{Median}I/B)_{PS11} = 34.9$$

A measure of central tendency, for example arithmetic mean, other means or median is then determined for the I/B ratio for each probe set in the sample set in which RHD exon 05 is known to be absent. In this case the measure of central tendency was the median (aMedian I/B).

$$a\mathrm{Median}I/B = \mathrm{Median}\ [p(I/B)_1, \ldots, p(I/B)_m]$$

$$a(\mathrm{Median}I/B)_{PS1} = 1.4$$

$$a(\mathrm{Median}I/B)_{PS2} = 5.3$$

$$a(\mathrm{Median}I/B)_{PS3} = 1.9$$

$$a(\mathrm{Median}I/B)_{PS4} = 3.7$$

$$a(\mathrm{Median}I/B)_{PS5} = 2.7$$

$$a(\mathrm{Median}I/B)_{PS6} = 1.3$$

$$a(\mathrm{Median}I/B)_{PS7} = 1.2$$

$$a(\mathrm{Median}I/B)_{PS8} = 1.2$$

$$a(\mathrm{Median}I/B)_{PS9} = 1.5$$

$$a(\mathrm{Median}I/B)_{PS10} = 2.0$$

$$a(\mathrm{Median}I/B)_{PS11} = 1.1$$

The sum of the measure of central tendency, for example arithmetic mean, other means or median for I/B ratios (in this case the sum of the medians (M)) was then determined, i.e. the ratio for the sample set in which RHD exon 05 is known to be present plus the ratio for the sample set in which RHD exon 05 is known to be absent, by probe set.

$$M = p\mathrm{Median}I/B + a\mathrm{Median}I/B$$

$$M_{PS1} = 5.4 + 1.4 = 6.8$$

$$M_{PS2} = 65.3 + 5.3 = 70.6$$

$$M_{PS3} = 26.7 + 1.9 = 28.6$$

$$M_{PS4} = 56.1 + 3.7 = 59.8$$

$$M_{PS5} = 48.1 + 2.7 = 51.5$$

$$M_{PS6} = 21.9 + 1.3 = 23.2$$

$$M_{PS7} = 22.4 + 1.6 = 24.1$$

$$M_{PS8} = 23.1 + 1.2 = 24.4$$

$$M_{PS9} = 45.7 + 1.5 = 47.2$$

$$M_{PS10} = 37.4 + 2.0 = 39.4$$

$$M_{PS11} = 34.9 + 1.1 = 36.0$$

The probe set score (S) for each probe set was then determined by dividing the amplitude of the interval (A) by the sum of measure of central tendency, for example arithmetic mean, other means or median for I/B ratios (M) (in this case the measure of central tendency was the median):

$$S = A/M = \frac{p(I/B)_1 - a(I/B)_m}{pMedian\ I/B + aMedian\ I/B}$$

$S_{PS1} = -2.2/6.8 = -0.33$ $S_{PS2} = -10.3/70.6 = -0.15$ $S_{PS3} = 0.0/28.6 = 0.00$ $S_{PS4} = -4.4/59.8 = -0.07$ $S_{PS5} = 2.1/51.5 = 0.04$ $S_{PS6} = 4.5/23.2 = 0.19$ $S_{PS7} = 1.85/24.1 = 0.08$ $S_{PS8} = 5.15/24.4 = 0.21$ $S_{PS9} = 14.81/47.2 = 0.31$ $S_{PS10} = 2.99/39.4 = 0.08$ $S_{PS11} = 12.94/36.0 = 0.36$

Based on their higher scores, two probe sets, PS9 and PS11 were selected for the determination of presence versus absence of RHD exon 05. However, a different number of probe sets (essentially any number) equal or higher than one may be selected.

Figure 1B:
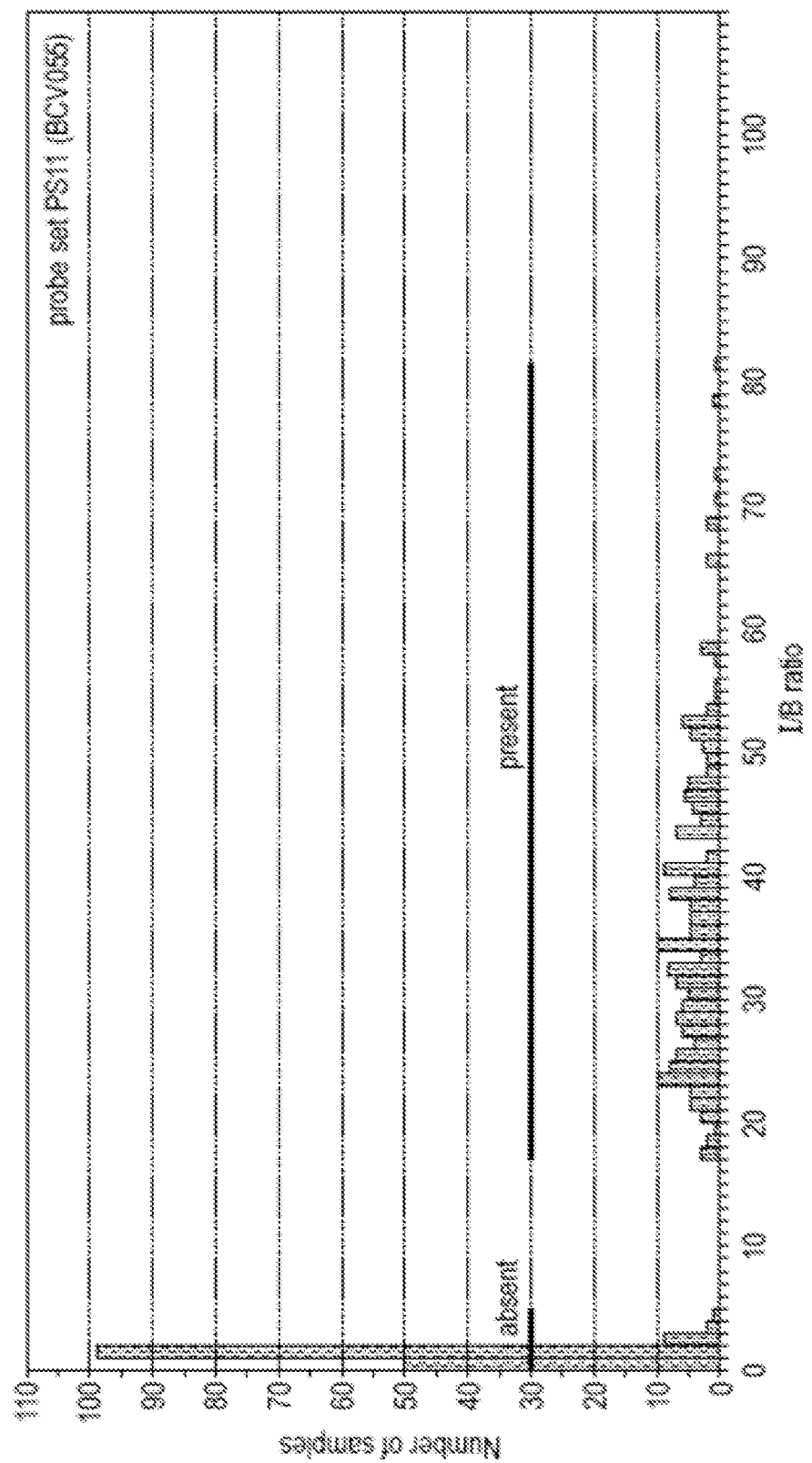

FIGS. 1A and 1B show, for optimal probe sets PS9 and PS11 (Blood Group Genotyping IDs BCV053 and BCV055, respectively), the frequency of samples in the reference sample set as a function of their I/B ratio.

The weighted I/B ratio threshold ($T_{I/B}$) that separates the I/B ratios of samples in which RHD exon 05 is known to be present from the I/B ratios of samples in which RHD exon 05 is known to be absent, was then determined by optimal probe set according to the following formula:

$$T_{I/B} = \frac{pMedian\ I/B \cdot a(I/B)_n - aMedian\ I/B \cdot p(I/B)_1}{pMedian\ I/B + a(I/B)_n - aMedian\ I/B - p(I/B)_1}$$

$$T_{I/B\ PS9} = \frac{45.7 \cdot 5.9 - 1.5 \cdot 20.7}{45.7 + 5.9 - 1.5 - 20.7} = 8.1$$

$$T_{I/B\ PS11} = \frac{34.9 \cdot 4.5 - 1.1 \cdot 17.4}{34.9 + 4.5 - 1.1 - 17.4} = 6.6$$

The upper boundary ($U_{NC}$) of the "No Call" region was then determined, for each optimal probe set, according to the following formula:

$$U_{NC} = \frac{T_{I/B} \cdot [pMedian\ I/B - 2 \cdot p(I/B)_1] + p(I/B)_1^2}{pMedian\ I/B - T_{I/B}}$$

$$U_{NC\ PS9} = \frac{8.1 \cdot (45.7 - 2 \cdot 20.7) + 20.7^2}{45.7 - 8.1} = 12.3$$

$$U_{NC\ PS11} = \frac{6.6 \cdot (34.9 - 2 \cdot 17.4) + 17.4^2}{34.9 - 6.6} = 10.8$$

The lower boundary of the "No Call" region was then determined, for each optimal probe set, according to the following formula:

$$L_{NC} = \frac{T_{I/B} \cdot [2 \cdot a(I/B)_n - aMedian\ I/B] - a(I/B)_n^2}{T_{I/B} - aMedian\ I/B}$$

$$L_{NC\ PS9} = \frac{8.1 \cdot (2 \cdot 5.9 - 1.5) - 5.9^2}{8.1 - 1.5} = 7.3$$

$$L_{NC\ PS11} = \frac{6.6 \cdot (2 \cdot 4.5 - 1.1) - 4.5^2}{6.6 - 1.1} = 5.8$$

Figure 2A:
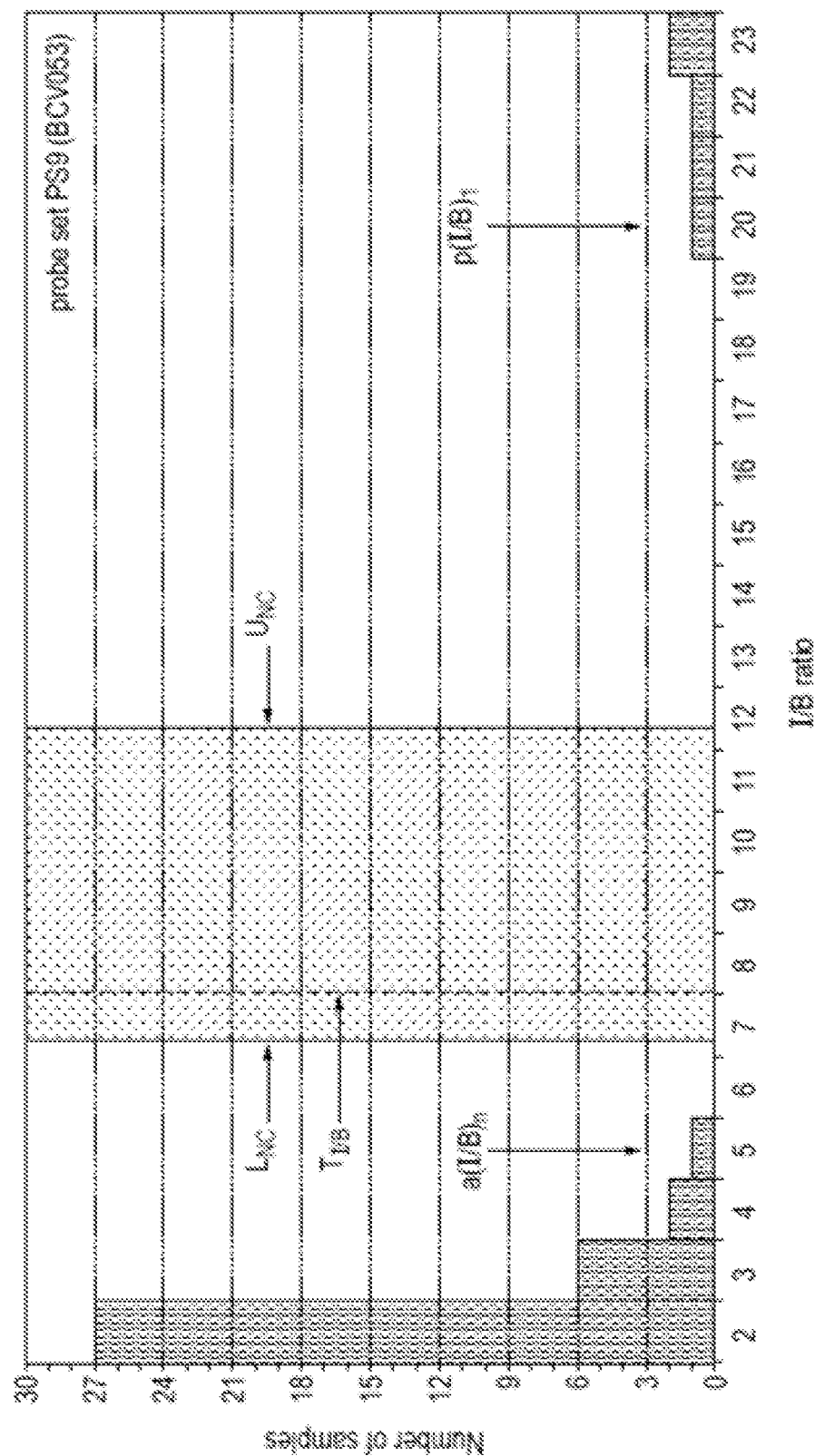
FIGS. 2A and B show in detail the transition region determined from I/B ratios of samples in which RHD exon 05 is known to be absent (left-hand side) to I/B ratios of samples in which it is known to be present (right-hand side) for optimal probe sets A) PS9 and B) PS11 (Blood Group Genotyping IDs BCV053 and BCV055, respectively). The shaded area shows the "No Call" region bounded by the lower boundary ($L_{NC}$) and the upper boundary ($U_{NC}$), with the weighted I/B ratio threshold ($T_{I/B}$) indicated by the dashed vertical line.
Figure 2B:
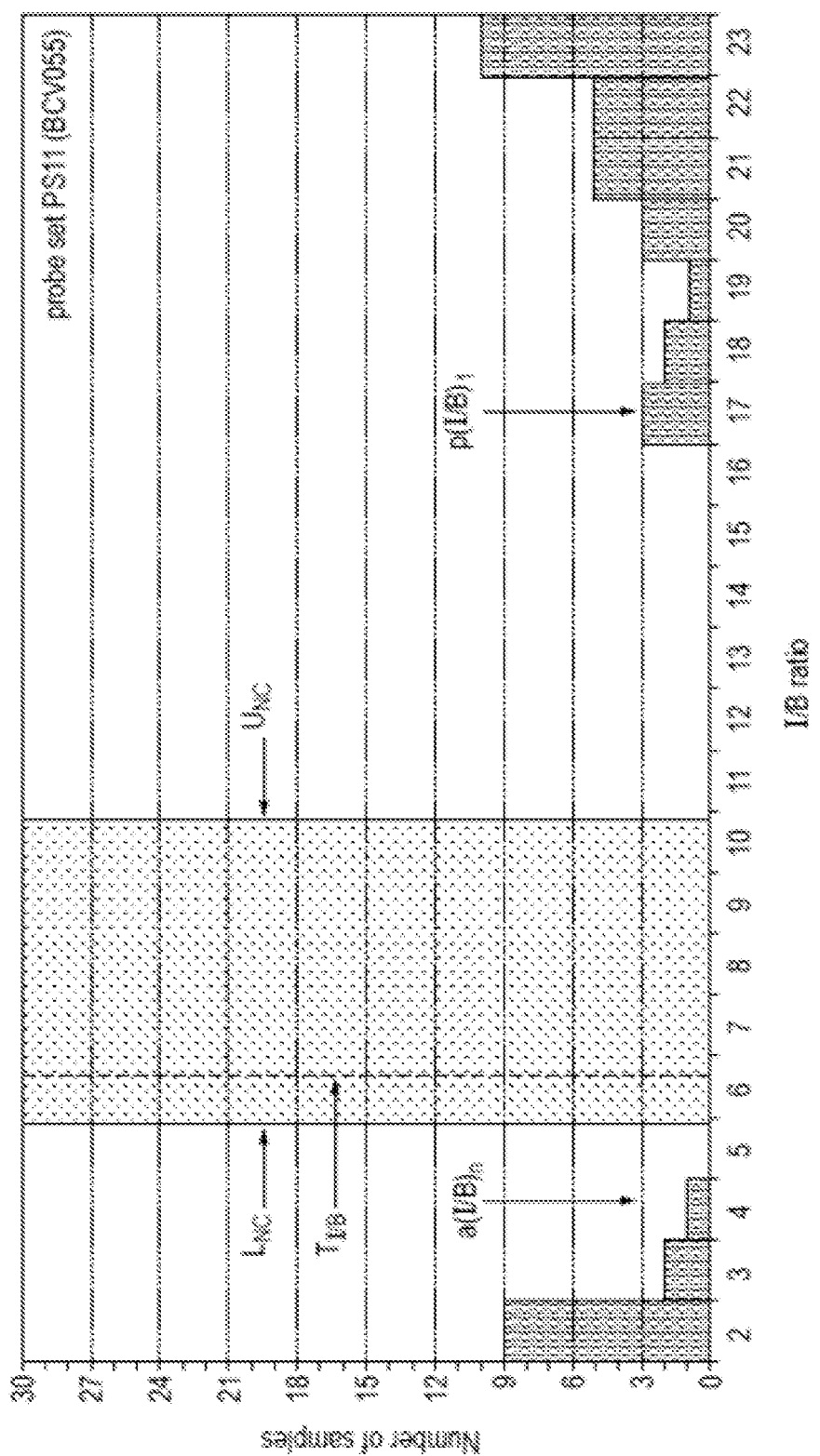

FIGS. 2A and 2B show in detail the transition region from I/B ratios of samples in which RHD exon 05 is known to be absent to I/B ratios of samples in which it is known to be present.

The I/B ratios were then obtained for each of the 358 test samples using the selected optimal probe sets (PS9 and PS11)

I/B ratios of the 358 test samples, by optimal probe set:

I/B$_{PS9}$: 0.7, 0.7, 0.8, 0.8, 0.8, 0.8, 0.8, 0.9, 0.9, 0.9, 0.9, 0.9, 0.9, 0.9, 1.0, 1.0, 1.0, 1.0, 1.0, 1.0, 1.0, 1.0, 1.0, 1.0, 1.0, 1.0, 1.0, 1.1, 1.1, 1.1, 1.1, 1.1, 1.1, 1.1, 1.1, 1.1, 1.1, 1.1, 1.1, 1.1, 1.1, 1.1, 1.2, 1.2, 1.2, 1.2, 1.2, 1.2, 1.2, 1.2, 1.2, 1.2, 1.2, 1.3, 1.3, 1.3, 1.3, 1.3, 1.3, 1.3, 1.3, 1.3, 1.3, 1.3, 1.3, 1.3, 1.4, 1.4, 1.4, 1.4, 1.4, 1.4, 1.4, 1.4, 1.4, 1.4, 1.5, 1.5, 1.5, 1.5, 1.5, 1.5, 1.5, 1.5, 1.5, 1.5, 1.5, 1.6, 1.6, 1.6, 1.6, 1.6, 1.6, 1.6, 1.6, 1.6, 1.6, 1.6, 1.6, 1.6, 1.7, 1.7, 1.7, 1.7, 1.8, 1.8, 1.8, 1.8, 1.8, 1.8, 1.8, 1.8, 1.9, 1.9, 1.9, 1.9, 2.0, 2.0, 2.0, 2.0, 2.1, 2.1, 2.1, 2.1, 2.1, 2.1, 2.1, 2.2, 2.2, 2.3, 2.3, 2.3, 2.4, 2.4, 2.5, 2.5, 2.5, 2.5, 2.5, 2.6, 2.7, 2.8, 2.8, 2.8, 2.8, 2.8, 3.0, 3.3, 3.4, 3.4, 3.5, 3.5, 3.8, 4.2, 4.8, 5.9, 20.7, 21.1, 22.9, 23.4, 23.8, 25.2, 26.1, 27.1, 27.2, 27.5, 28.8, 28.9, 29.5, 29.7, 29.7, 30.1, 30.3, 30.4, 30.6, 30.6, 30.9, 30.9, 31.0, 31.3, 31.6, 31.6, 31.7, 31.8, 31.8, 32.3, 32.4, 32.5, 33.0, 33.2, 33.8, 34.5, 35.1, 35.1, 35.6, 35.6, 36.1, 36.2, 36.2, 36.7, 36.7, 36.8, 37.1, 37.1, 37.1, 38.1, 38.4, 38.5, 38.6, 38.9, 39.1, 39.3, 39.5, 39.6, 39.6, 39.7, 39.9, 39.9, 39.9, 40.0, 40.0, 40.3, 40.4, 40.8, 40.9, 41.0, 41.2, 41.5, 41.5, 41.6, 41.8, 42.0, 42.0, 42.4, 42.5, 42.9, 42.9, 42.9, 42.9, 43.0, 43.1, 43.2, 43.2, 43.3, 43.6, 43.6, 43.8, 44.0, 44.1, 44.2, 44.4, 45.4, 45.6, 45.7, 45.7, 45.8, 46.2, 46.4, 46.8, 46.9, 47.4, 47.5, 47.7, 47.9, 47.9, 48.5, 48.6, 48.8, 48.9, 48.9, 49.2, 49.4, 50.4, 50.7, 50.8, 51.0, 51.3, 51.6, 52.9, 53.3, 53.4, 53.5, 53.8, 54.1, 54.2, 55.2, 55.7, 56.5, 57.0, 57.5, 58.7, 59.0, 59.4, 59.6, 60.6, 61.5, 61.6, 61.8, 62.6, 62.9, 63.0, 63.3, 63.5, 64.0, 64.2, 64.6, 64.9, 65.1, 65.3, 65.3, 65.3, 65.7, 65.7, 65.8, 65.8, 66.4, 67.7, 67.7, 67.8, 67.8, 68.5, 69.8, 69.9, 69.9, 70.2, 71.3, 71.4, 71.7, 73.0, 73.0, 73.3, 73.5, 73.5, 73.9, 74.9, 74.9, 75.8, 75.8, 75.8, 76.6, 76.6, 76.8, 77.7, 78.4, 78.9, 80.2, 86.0, 91.1, 91.3, 94.5, 96.2, 99.8, 108.6

I/B$_{PS11}$: 0.5, 0.6, 0.6, 0.6, 0.7, 0.7, 0.7, 0.8, 0.8, 0.8, 0.8, 0.8, 0.8, 0.8, 0.8, 0.8, 0.8, 0.8, 0.8, 0.8, 0.8, 0.8, 0.8, 0.8, 0.9, 0.9, 0.9, 0.9, 0.9, 0.9, 0.9, 0.9, 0.9, 0.9, 0.9, 0.9, 0.9, 0.9, 1.0, 1.0, 1.0, 1.0, 1.0, 1.0, 1.0, 1.0, 1.0, 1.0, 1.0, 1.0, 1.0, 1.0, 1.0, 1.0, 1.0, 1.0, 1.0, 1.0, 1.0, 1.1, 1.1, 1.1, 1.1, 1.1, 1.1, 1.1, 1.1, 1.1, 1.1, 1.1, 1.1, 1.1, 1.1, 1.1, 1.1, 1.1, 1.1, 1.1, 1.1, 1.1, 1.1, 1.1, 1.1, 1.1, 1.1, 1.1, 1.1, 1.1, 1.1, 1.1, 1.1, 1.1, 1.2, 1.2, 1.2, 1.2, 1.2, 1.2, 1.2, 1.2, 1.2, 1.2, 1.2, 1.2, 1.2, 1.2, 1.3, 1.3, 1.3, 1.3, 1.3, 1.3, 1.3, 1.3, 1.3, 1.3, 1.3, 1.4, 1.4, 1.4, 1.4, 1.4, 1.4, 1.4, 1.4, 1.5, 1.5, 1.5, 1.5, 1.5, 1.5, 1.5, 1.5, 1.6, 1.6, 1.6, 1.6, 1.7, 1.7, 1.7, 1.7, 1.7, 1.8, 1.8, 1.8, 1.9, 1.9, 2.0, 2.0, 2.0, 2.1, 2.1, 2.1, 2.2, 2.3, 2.5, 3.0, 3.1, 3.4, 4.5, 17.4, 17.8, 18.0, 18.5, 18.9, 19.3, 20.2, 20.3, 21.0, 21.0, 21.2, 21.3, 21.6, 22.0, 22.0, 22.6, 22.7, 22.8, 23.0, 23.1, 23.3, 23.5, 23.5, 23.6, 23.7, 23.7, 23.8, 24.0, 24.0, 24.0, 24.1, 24.4, 24.7, 24.7, 24.9, 24.9, 25.2, 25.2, 25.7, 25.7, 25.8, 25.8, 25.8, 26.6, 26.6, 26.7, 26.7, 27.4, 27.6, 27.7, 27.8, 27.8, 27.9, 28.1, 28.1, 28.4, 28.5, 28.6, 28.7, 28.7, 29.2, 29.5, 29.6, 29.7, 29.9, 29.9, 30.2, 30.3, 30.8, 30.9, 30.9, 31.1, 31.2, 31.4, 31.4, 31.5, 31.7, 31.9, 32.1, 32.2, 32.3, 32.4, 32.5, 32.7, 32.8, 32.8, 33.4, 33.4, 33.9, 34.0, 34.1, 34.2, 34.4, 34.6, 34.7, 34.8, 34.9, 34.9, 35.0, 35.3, 35.6, 35.6, 35.7, 35.7, 36.4, 36.5, 36.7, 36.7, 36.9, 37.1, 37.1, 37.3, 37.4, 37.5, 38.1, 38.2, 38.2, 38.4, 38.7, 38.9, 38.9, 38.9, 39.5, 39.5, 39.8, 39.9, 40.0, 40.1, 40.2, 40.3, 40.3, 40.4, 40.6, 40.8, 41.0, 41.0, 41.9, 43.0, 43.0, 43.1, 43.2, 43.2, 43.7, 43.8, 44.1, 44.3, 44.4, 45.3, 45.4, 45.6, 45.9, 46.0, 46.0, 46.2, 46.5, 46.5, 46.7, 47.1, 47.7, 47.7, 47.8, 47.8, 48.3, 48.6, 49.6, 49.8, 50.3, 50.5, 50.9, 51.3, 51.5, 51.5, 51.7, 51.8, 52.0, 52.1, 52.4, 52.4, 52.6, 52.7, 53.0, 53.6, 54.3, 55.0, 57.8, 58.1, 58.5, 58.7, 65.6, 65.9, 68.5, 68.8, 70.4, 72.6, 78.7, 81.4

The following determination was then made to detect the presence versus the absence of RHD exon 05 in each of a mixed set of 358 samples. This mixed set of sample was the result of pooling the reference samples used above, in which RHD exon 05 is known to be either present (197 samples) or absent (161 samples), i.e. 197+161=358 samples.

I/B ratios of samples for which RHD exon 05 is found absent ($PS_9$ I/B<$L_{NC}$, $PS_{11}$ I/B<$L_{NC}$), by probe set:

$Absent_{PS9}$: 0.7, 0.7, 0.8, 0.8, 0.8, 0.8, 0.8, 0.9, 0.9, 0.9, 0.9, 0.9, 0.9, 0.9, 1.0, 1.0, 1.0, 1.0, 1.0, 1.0, 1.0, 1.0, 1.0, 1.0, 1.0, 1.0, 1.1, 1.1, 1.1, 1.1, 1.1, 1.1, 1.1, 1.1, 1.1, 1.1, 1.1, 1.1, 1.1, 1.1, 1.1, 1.1, 1.2, 1.2, 1.2, 1.2, 1.2, 1.2, 1.2, 1.2, 1.2, 1.2, 1.2, 1.3, 1.3, 1.3, 1.3, 1.3, 1.3, 1.3, 1.3, 1.3, 1.3, 1.3, 1.3, 1.3, 1.4, 1.4, 1.4, 1.4, 1.4, 1.4, 1.4, 1.4, 1.4, 1.4, 1.4, 1.5, 1.5, 1.5, 1.5, 1.5, 1.5, 1.5, 1.5, 1.5, 1.5, 1.5, 1.6, 1.6, 1.6, 1.6, 1.6, 1.6, 1.6, 1.6, 1.6, 1.6, 1.6, 1.6, 1.6, 1.6, 1.7, 1.7, 1.7, 1.7, 1.8, 1.8, 1.8, 1.8, 1.8, 1.8, 1.8, 1.8, 1.9, 1.9, 1.9, 1.9, 2.0, 2.0, 2.0, 2.0, 2.1, 2.1, 2.1, 2.1, 2.1, 2.1, 2.1, 2.2, 2.2, 2.3, 2.3, 2.3, 2.4, 2.4, 2.5, 2.5, 2.5, 2.5, 2.5, 2.6, 2.7, 2.8, 2.8, 2.8, 2.8, 2.8, 3.0, 3.3, 3.4, 3.4, 3.5, 3.5, 3.8, 4.2, 4.8, 5.9

$Absent_{PS11}$: 0.5, 0.6, 0.6, 0.6, 0.7, 0.7, 0.7, 0.8, 0.8, 0.8, 0.8, 0.8, 0.8, 0.8, 0.8, 0.8, 0.8, 0.8, 0.8, 0.8, 0.8, 0.8, 0.8, 0.9, 0.9, 0.9, 0.9, 0.9, 0.9, 0.9, 0.9, 0.9, 0.9, 0.9, 0.9, 0.9, 0.9, 1.0, 1.0, 1.0, 1.0, 1.0, 1.0, 1.0, 1.0, 1.0, 1.0, 1.0, 1.0, 1.0, 1.0, 1.0, 1.0, 1.0, 1.0, 1.0, 1.0, 1.0, 1.1, 1.1, 1.1, 1.1, 1.1, 1.1, 1.1, 1.1, 1.1, 1.1, 1.1, 1.1, 1.1, 1.1, 1.1, 1.1, 1.1, 1.1, 1.1, 1.1, 1.1, 1.1, 1.1, 1.1, 1.1, 1.1, 1.2, 1.2, 1.2, 1.2, 1.2, 1.2, 1.2, 1.2, 1.2, 1.2, 1.2, 1.2, 1.2, 1.2, 1.2, 1.2, 1.3, 1.3, 1.3, 1.3, 1.3, 1.3, 1.3, 1.3, 1.3, 1.3, 1.4, 1.4, 1.4, 1.4, 1.4, 1.4, 1.4, 1.4, 1.5, 1.5, 1.5, 1.5, 1.5, 1.5, 1.5, 1.5, 1.6, 1.6, 1.6, 1.6, 1.7, 1.7, 1.7, 1.7, 1.8, 1.8, 1.8, 1.9, 1.9, 2.0, 2.0, 2.0, 2.1, 2.1, 2.1, 2.2, 2.3, 2.5, 3.0, 3.1, 3.4, 4.5

I/B ratios of samples for which RHD exon 05 is found present ($PS_9$ I/B>$U_{NC}$, $PS_{11}$ I/B>$U_{NC}$), by probe set:

$Present_{PS9}$: 17.4, 17.8, 18.0, 18.5, 18.9, 19.3, 20.2, 20.3, 21.0, 21.0, 21.2, 21.3, 21.6, 22.0, 22.0, 22.6, 22.7, 22.8, 23.0, 23.1, 23.3, 23.5, 23.5, 23.5, 23.6, 23.7, 23.7, 23.8, 24.0, 24.0, 24.0, 24.1, 24.4, 24.7, 24.7, 24.9, 24.9, 25.2, 25.2, 25.7, 25.7, 25.8, 25.8, 25.8, 26.6, 26.6, 26.7, 26.7, 27.4, 27.6, 27.7, 27.8, 27.8, 27.9, 28.1, 28.1, 28.4, 28.5, 28.6, 28.7, 28.7, 29.2, 29.5, 29.6, 29.7, 29.9, 29.9, 30.2, 30.3, 30.8, 30.9, 30.9, 31.1, 31.2, 31.4, 31.4, 31.5, 31.7, 31.9, 32.1, 32.2, 32.3, 32.4, 32.5, 32.7, 32.8, 32.8, 33.4, 33.4, 33.9, 34.0, 34.1, 34.2, 34.4, 34.6, 34.7, 34.8, 34.9, 34.9, 35.0, 35.3, 35.6, 35.6, 35.7, 35.7, 36.4, 36.5, 36.7, 36.7, 36.9, 37.1, 37.1, 37.3, 37.4, 37.5, 38.1, 38.2, 38.2, 38.4, 38.7, 38.9, 38.9, 38.9, 39.5, 39.5, 39.8, 39.9, 40.0, 40.1, 40.2, 40.3, 40.3, 40.4, 40.6, 40.8, 41.0, 41.0, 41.9, 43.0, 43.0, 43.1, 43.2, 43.2, 43.7, 43.8, 44.1, 44.3, 44.4, 45.3, 45.4, 45.6, 45.9, 46.0, 46.0, 46.2, 46.5, 46.5, 46.7, 47.1, 47.7, 47.7, 47.8, 47.8, 48.3, 48.6, 49.6, 49.8, 50.3, 50.5, 50.9, 51.3, 51.5, 51.5, 51.7, 51.8, 52.0, 52.1, 52.4, 52.4, 52.6, 52.7, 53.0, 53.6, 54.3, 55.0, 57.8, 58.1, 58.5, 58.7, 65.6, 65.9, 68.5, 68.8, 70.4, 72.6, 78.7, 81.4

$Present_{PS11}$: 17.4, 17.8, 18.0, 18.5, 18.9, 19.3, 20.2, 20.3, 21.0, 21.0, 21.2, 21.3, 21.6, 22.0, 22.0, 22.6, 22.7, 22.8, 23.0, 23.1, 23.3, 23.5, 23.5, 23.5, 23.6, 23.7, 23.7, 23.8, 24.0, 24.0, 24.0, 24.1, 24.4, 24.7, 24.7, 24.9, 24.9, 25.2, 25.2, 25.7, 25.7, 25.8, 25.8, 25.8, 26.6, 26.6, 26.7, 26.7, 27.4, 27.6, 27.7, 27.8, 27.8, 27.9, 28.1, 28.1, 28.4, 28.5, 28.6, 28.7, 28.7, 29.2, 29.5, 29.6, 29.7, 29.9, 29.9, 30.2, 30.3, 30.8, 30.9, 30.9, 31.1, 31.2, 31.4, 31.4, 31.5, 31.7, 31.9, 32.1, 32.2, 32.3, 32.4, 32.5, 32.7, 32.8, 32.8, 33.4, 33.4, 33.9, 34.0, 34.1, 34.2, 34.4, 34.6, 34.7, 34.8, 34.9, 34.9, 35.0, 35.3, 35.6, 35.6, 35.7, 35.7, 36.4, 36.5, 36.7, 36.7, 36.9, 37.1, 37.1, 37.3, 37.4, 37.5, 38.1, 38.2, 38.2, 38.4, 38.7, 38.9, 38.9, 38.9, 39.5, 39.5, 39.8, 39.9, 40.0, 40.1, 40.2, 40.3, 40.3, 40.4, 40.6, 40.8, 41.0, 41.0, 41.9, 43.0, 43.0, 43.1, 43.2, 43.2, 43.7, 43.8, 44.1, 44.3, 44.4, 45.3, 45.4, 45.6, 45.9, 46.0, 46.0, 46.2, 46.5, 46.5, 46.7, 47.1, 47.7, 47.7, 47.8, 47.8, 48.3, 48.6, 49.6, 49.8, 50.3, 50.5, 50.9, 51.3, 51.5, 51.5, 51.7, 51.8, 52.0, 52.1, 52.4, 52.4, 52.6, 52.7, 53.0, 53.6, 54.3, 55.0, 57.8, 58.1, 58.5, 58.7, 65.6, 65.9, 68.5, 68.8, 70.4, 72.6, 78.7, 81.4

The determination of presence/absence of RHD exon 05 in the 358 test samples, by both probe sets combined (PS9•PS11) yielded the following:

$Absent_{PS9 \cdot PS11}$: samples 1-161

$Present_{PS9 \cdot PS11}$: samples 162-358

By following the process described above, a correct determination is made for 197 out of 197 samples (100%) in which RHD exon 05 is present, and 161 samples out of 161 samples (100%) in which RHD exon 05 is absent. No sample was classified as a "No Call". All calls made using the two optimal probe sets agree with the known absent/present status of RHD exon 05 in the sample set. The results therefore demonstrate the reliability of the method of the present invention.

Table 4 below lists the sequences of the oligonucleotide probes used to interrogate the two allelic variants at one or more polymorphic positions in each one of the 10 exons of the RHD gene. These probes may be used both, to interrogate allelic variants within their cognate sequence, and to determine the presence or absence of the RHD exon in which their cognate sequence is located.

TABLE 4

RHD Probe Sequences

| RHD exon | Polymorphism | Allelic variant | Probe Sequence | SEQ ID NO. |
|---|---|---|---|---|
| #01 | #1 | #1 | CCTGCCCCTCTGGGCCCTAACACTG | 1. |
| #01 | #1 | #2 | CCTGCCCCTCTGAGCCCTAACACTG | 2. |
| #01 | #1 | #2 | CCTGCCCCTCTGAGCACTAACACTG | 3. |
| #01 | #2 | #1 | CCTGCCCCTCTGGGCCCTAACACTG | 1. |

TABLE 4 -continued

RHD Probe Sequences

| RHD exon | Polymorphism | Allelic variant | Probe Sequence | SEQ ID NO. |
|---|---|---|---|---|
| #01 | #2 | #2 | CCTGCCCCTCTGCGACCTAACACTG | 4. |
| #01 | #2 | #2 | CCTGCCCCTCTGCGCACTAACACTG | 5. |
| #02 | #1 | #1 | GGTCATCACACTGTTCAGGTATT | 6. |
| #02 | #1 | #1 | TGGTCATCACACTGTTCAGGTATTG | 7. |
| #02 | #1 | #2 | GGTCATCACACCGTTCAGGTATT | 8. |
| #02 | #1 | #2 | TGGTCATCACACCGTTCAGGTATTG | 9. |
| #02 | #2 | #1 | GTCATCACACTGTTCAGGTATTG | 10. |
| #02 | #2 | #2 | GTCATCACACTTCAGGTATTGGG | 11. |
| #03 | #1 | #1 | CCCAGTATTCGGCTGGCCACCATGA | 12. |
| #03 | #1 | #1 | CCAGTATTCGGCTGGCCACCATG | 13. |
| #03 | #1 | #2 | CCCAGTATTCGGTGGCCACCATGAG | 14. |
| #03 | #1 | #2 | CCAGTATTCGGTGGCCACCATGA | 15. |
| #03 | #2 | #1 | AGGTGACAGCTTTAGGCAACCTGAG | 16. |
| #03 | #2 | #2 | AGGTGACAGCTTAGGCAACCTGAGG | 17. |
| #04 | #1 | #1 | ACATGAACATGATGCACATCTACGT | 18. |
| #04 | #1 | #1 | CATGAACATGATGCACATCTACG | 19. |
| #04 | #1 | #2 | ACATGAACATGACGCACATCTACGT | 20. |
| #04 | #1 | #2 | CATGAACATGACGCACATCTACG | 21. |
| #04 | #2 | #1 | AACATGATGCACATCTACGTGTTCG | 22. |
| #04 | #2 | #1 | ACATGATGCACATCTACGTGTTC | 23. |
| #04 | #2 | #2 | AACCTGAGGCACTTCTACGTGTTCG | 24. |
| #04 | #2 | #2 | ACCTGAGGCACTTCTACGTGTTC | 25. |
| #05 | #1 | #1 | AGGAAGAATGCCGTGTTCAACAC | 26. |
| #05 | #1 | #2 | AGGAAGAATGCGTGTTCAACACC | 27. |
| #05 | #2 | #1 | GGCTCACCCCCAAGGGAAGGGAAGA | 28. |
| #05 | #2 | #2 | GGCTCACCCCCAGGGAAGGGAAGAT | 29. |
| #06 | #1 | #1 | ATGGTGTTCTCTCTCTACCTTGCTT | 30. |
| #06 | #1 | #1 | TGGTGTTCTCTCTCTACCTTGCT | 31. |
| #06 | #1 | #2 | ATGGTGTTCTCTACCTTGCTTCCTT | 32. |
| #06 | #1 | #2 | TGGTGTTCTCTACCTTGCTTCCT | 33. |
| #06 | #2 | #1 | TTTGCAGACTTATGTGCACAGTGCG | 34. |
| #06 | #2 | #1 | TTGCAGACTTATGTGCACAGTGC | 35. |
| #06 | #2 | #2 | TTTGCAGACTTAGGTGCACAGTGCG | 36. |
| #06 | #2 | #2 | TTGCAGACTTATGTGCACAGTGC | 37. |
| #06 | #3 | #1 | TTTGCAGACTTATGTGCACAGTGCG | 34. |
| #06 | #3 | #1 | TTGCAGACTTATGTGCACAGTGC | 35. |
| #06 | #3 | #2 | TTTGCAGACTTAAGTGCACAGTGCG | 38. |
| #06 | #3 | #2 | TTGCAGACTTATGTGCACAGTGC | 39. |

TABLE 4-continued

RHD Probe Sequences

| RHD exon | Polymorphism | Allelic variant | Probe Sequence | SEQ ID NO. |
|---|---|---|---|---|
| #06 | #4 | #1 | GCAGACTTATGTGCACAGTGCGG | 40. |
| #06 | #4 | #1 | CAGACTTATGTGCACAGTGCG | 41. |
| #06 | #4 | #2 | GCAGACTTATGGGCACAGTGCGG | 42. |
| #06 | #4 | #2 | CAGACTTATGGGCACAGTGCG | 43. |
| #06 | #5 | #1 | TTGGCAGGAGGCGTGGCTGTG | 44. |
| #06 | #5 | #1 | ACAGCCACGCCTCCTGCCA | 45. |
| #06 | #5 | #2 | TTGGCAGGAGACGTGGCTGTG | 46. |
| #06 | #5 | #2 | ACAGCCACGTCTCCTGCCA | 47. |
| #06 | #6 | #1 | GCGTGGCTGTGGGTACCTCGTGTCA | 48. |
| #06 | #6 | #1 | CGTGGCTGTGGGTACCTCGTGTC | 49. |
| #06 | #6 | #2 | GCGTGGCTGTGGATACCTCGTGTCA | 50. |
| #06 | #6 | #2 | CGTGGCTGTGGATACCTCGTGTC | 51. |
| #06 | #7 | #1 | GGCTGTGGGTACCTCGTGTCACC | 52. |
| #06 | #7 | #1 | GCTGTGGGTACCTCGTGTCAC | 53. |
| #06 | #7 | #2 | GGCTGTGGGTATCTCGTGTCACC | 54. |
| #06 | #7 | #2 | GCTGTGGGTATCTCGTGTCAC | 55. |
| #06 | #8 | #1 | TGGGTACCTCGTGTCACCTGATCCC | 56. |
| #06 | #8 | #1 | GGGTACCTCGTGTCACCTGATCC | 57. |
| #06 | #8 | #2 | TGGGTACCTCGTATCACCTGATCCC | 58. |
| #06 | #8 | #2 | GGGTACCTCGTATCACCTGATCC | 59. |
| #06 | #9 | #1 | GGCTTGCCATGGTGCTGGGTC | 60. |
| #06 | #9 | #1 | GCTTGCCATGGTGCTGGGT | 61. |
| #06 | #9 | #2 | GGCTTGCCATTGTGCTGGGTC | 62. |
| #06 | #9 | #2 | GCTTGCCATTGTGCTGGGT | 63. |
| #06 | #10 | #1 | GTGGCTGGGCTGATCTCCGTCGG | 64. |
| #06 | #10 | #1 | TGGCTGGGCTGATCTCCGTCG | 65. |
| #06 | #10 | #2 | GTGGCTGGGCTTGGCTGATCTCC | 66. |
| #06 | #10 | #2 | TGGCTGGGCTTGGCTGATCTC | 67. |
| #06 | #11 | #1 | GGCTGATCTCCGTCGGGGAGCC | 68. |
| #06 | #11 | #1 | GCTGATCTCCGTCGGGGAGC | 69. |
| #06 | #11 | #2 | GGCTGATCTCCATCGGGGAGCC | 70. |
| #06 | #11 | #2 | GCTGATCTCCATCGGGGAGC | 71. |
| #06 | #12 | #1 | GGAGCCAAGTACCTGCCGGTAAG | 72. |
| #06 | #12 | #1 | GAGCCAAGTACCTGCCGGTAA | 73. |
| #06 | #12 | #2 | GGAGCCAAGTAACTGCCGGTAAG | 74. |
| #06 | #12 | #2 | GAGCCAAGTAACTGCCGGTAA | 75. |
| #06 | #13 | #1 | AGTACCTGCCGGTAAGAAACTAGAC | 76. |

TABLE 4 -continued

RHD Probe Sequences

| RHD exon | Polymorphism | Allelic variant | Probe Sequence | SEQ ID NO. |
|---|---|---|---|---|
| #06 | #13 | #1 | GTACCTGCCGGTAAGAAACTAGA | 77. |
| #06 | #13 | #2 | AGTACCTGCCGGAAACTAGACAACT | 78. |
| #06 | #13 | #2 | GTACCTGCCGGAAACTAGACAAC | 79. |
| #07 | #1 | #1 | TGGGTCTGCTTGGAGAGATCATCTA | 80. |
| #07 | #1 | #1 | GGGTCTGCTTGGAGAGATCATCT | 81. |
| #07 | #1 | #2 | TGGGTCTGCTTGAAGAGATCATCTA | 82. |
| #07 | #1 | #2 | GGGTCTGCTTGAAGAGATCATCT | 83. |
| #07 | #2 | #1 | CTGCTGGTGCTTGATACCGTCGGAG | 84. |
| #07 | #2 | #1 | TGCTGGTGCTTGATACCGTCGGA | 85. |
| #07 | #2 | #2 | CTGCTGGTGCTTCATACTGTCTGGA | 86. |
| #07 | #2 | #2 | TGCTGGTGCTTCATACTGTCTGG | 87. |
| #08 | #1 | #1 | GTCTCCTGACAGGTCAGTGTGAGGC | 88. |
| #08 | #1 | #1 | TCTCCTGACAGGTCAGTGTGAGG | 89. |
| #08 | #1 | #2 | GTCTCCTGACAGATCAGTGTGAGGC | 90. |
| #08 | #1 | #2 | TCTCCTGACAGATCAGTGTGAGG | 91. |
| #09 | #1 | #1 | GCATTTAAACAGGTTTGCTCCTAAA | 92. |
| #09 | #1 | #1 | TGCATTTAAACAGGTTTGCTC-CTAAAT | 93. |
| #09 | #1 | #2 | GCATTTAAACAGCTTTGCTCCTAAA | 94. |
| #09 | #1 | #2 | TGCATTTAAACAGCTTTGCTC-CTAAAT | 95. |
| #09 | #2 | #1 | TATTTTGATGACCAAGTTTTCTGGA | 96. |
| #09 | #2 | #1 | ATTTTGATGACCAAGTTTTCTGG | 97. |
| #09 | #2 | #2 | TATTTTGATGACTAAGTTTTCTGGA | 98. |
| #09 | #2 | #2 | ATTTTGATGACTAAGTTTTCTGG | 99. |
| #10 | #1 | #1 | GATGCTTTTGCTTAAAATCCAACAG | 100. |
| #10 | #1 | #2 | ATGCTTTTGCTTAAAAATCCAACAG | 101. |

All references cited herein are incorporated herein by reference in their entirety and for all purposes to the same extent as if each individual publication or patent or patent application was specifically and individually indicated to be incorporated by reference in its entirety.

The specific embodiments described herein are offered by way of example, not by way of limitation. Any sub-titles herein are included for convenience only, and are not to be construed as limiting the disclosure in any way.

REFERENCES

Botstein et al. (1980). Am. J. Hum. Genet. 32:314-331.
Chang et al. (1998). Blood 92:2602-2604.
Dutrillaux et al. (1990). Cancer Genet. Cytogenet. 49:203-217.
Hensel et al. (1990). Cancer Res. 50:3067.
Jin et al. (1993). Blood 82:2281-2288.
Kitano et al. (2000). American Genetic Association 91:211-214.
Mullis et al. (1986). Cold Spring Harbor Symp. Quant. Biol. 51:263-273.
Mullis K B and Faloona F A (1987). Methods Enzymol. 155:335-350.
Olerup O and Zetterquist H (1992). Tissue Antigens 39:225-235.
Sanger F and Coulson A R (1975). J. Mol. Biol. 94:441-448.
Smith et al. (1986). Nature 321:674-679.
Southern E M (1975). J Mol Biol. 98:503-517.
U.S. Pat. No. 6,599,701. Identifying organisms by detecting intronic nucleic acids.
PCT patent application no. WO 2010/008071. Method for screening of gene mutation by utilizing quantification technique.
PCT patent application no. WO 2001/018245. Detection of alterations in a gene by long range PCR using human mobile elements.

The invention claimed is:

1. A method for determining the presence or absence of a genetic segment of interest in a DNA-containing sample, the method comprising:
   (i) bringing at least a first probe set comprising a plurality of replicates of at least one oligonucleotide probe that interrogates a first cognate sequence within said segment of interest into contact with (a) a plurality of reference samples in which the genetic segment of interest is absent, and (b) a plurality of reference samples in which the genetic segment of interest is present, under conditions that allow probe-cognate sequence hybridisation to occur;
   (ii) measuring the intensity of probe-sample hybridisation of each of the reference samples, thereby obtaining a first cluster of hybridisation intensity values for the reference samples in which the genetic segment of interest is absent and a second cluster of hybridisation intensity values for the reference samples in which the genetic segment of interest is present; and
   (iii) establishing a "no call" region of hybridisation intensity values that lies in the region between said first and second clusters and which is bounded by a lower no call boundary ("LNC") and an upper no call boundary ("UNC"), wherein the LNC and UNC represent statistical confidence limits for assigning a hybridisation intensity value to said first and said second clusters, respectively;
   iv) contacting the first probe set with at least one DNA-containing test sample under conditions that allow probe-cognate sequence hybridisation to occur;
   v) measuring the intensity of probe-sample hybridisation of the at least one test sample; and
   vi) comparing the measured hybridisation intensity with the LNC and the UNC, wherein a measured hybridisation intensity below the LNC indicates that said genetic segment of interest is absent in the test sample and a measured hybridisation intensity above UNC indicates that said genetic segment of interest is present in the test sample; wherein:
   the DNA of the reference samples and/or the test sample has been labelled with a fluorescent label and wherein measuring hybridisation intensity comprises measuring the fluorescence signal of the fluorescent label at each oligonucleotide probe location;
   the hybridisation intensity for each probe set is measured as I/B, where:

I is determined as a measure of central tendency of the measured fluorescence signal of the replicates of each oligonucleotide probe; and B is determined as a measure of central tendency of the background fluorescence signal of the replicates of each oligonucleotide probe; and the LNC and UNC values are calculated according to the following formulae:

$$L_{NC} = \frac{T_{I/B} \cdot [2 \cdot a(I/B)_n - aMedian\ I/B] - a(I/B)_n^2}{T_{I/B} - aMedian\ I/B}$$

$$U_{NC} = \frac{T_{I/B} \cdot [pMedian\ I/B - 2 \cdot p(I/B)_1] + p(I/B)_1^2}{pMedian\ I/B - T_{I/B}}$$

where:

$$T_{I/B} = \frac{pMedian\ I/B \cdot a(I/B)_n - aMedian\ I/B \cdot p(I/B)_1}{pMedian\ I/B + a(I/B)_n - aMedian\ I/B - p(I/B)_1}$$

aMedianI/B is a measure of central tendency of the measured I/B values of the reference samples in which the genetic segment of interest is absent;

pMedianI/B is a measure of central tendency of the measured I/B values of the reference samples in which the genetic segment of interest is present;

a(I/B)n is the greatest measured I/B value of the reference samples in which the genetic segment of interest is absent; and p(I/B)1 is the lowest measured I/B value of the reference samples in which the genetic segment of interest is present.

2. A method according to claim 1, wherein said genetic segment of interest is selected from the group consisting of: an exon, an intron and a promoter.

3. A method according to claim 1, wherein at least a second probe set is employed in addition to said first probe set and wherein the second probe set comprises a plurality of replicates of at least one oligonucleotide probe that interrogates a second cognate sequence within said segment of interest, the method further comprising establishing a second no call region bounded by LNC and UNC boundaries for the second probe set.

4. A method according to claim 3, wherein the test sample is classified as having or not having said segment of interest based on a strict consensus between the determinations of the first and second probe sets.

5. A method according to claim 4, wherein said strict consensus is a strict consensus as set forth in Table 1.

6. A method according to claim 3, wherein the test sample is classified as having or not having said segment of interest based on a majority consensus between the determinations of the first and second probe sets in the absence of contradictory determinations.

7. A method according to claim 6, wherein said majority consensus is a majority consensus as set forth in Table 2.

8. A method according to claim 1, wherein the oligonucleotide probes are attached to a solid support.

9. A method according to claim 8, wherein the oligonucleotide probes are attached to a substantially planar solid support in the form of an array.

10. A method according to claim 8, wherein the oligonucleotide probes are attached to one or more particles.

11. A method according to claim 10, wherein said particles are selected from the group consisting of: micrometer-sized beads, nanometer-sized beads and cylinders.

12. A method according to claim 1, wherein said test sample comprises DNA amplified from genomic DNA of a test subject, which DNA has been fragmented and/or labelled with a detectable label.

13. A method according to claim 1, wherein each of the reference samples comprises DNA amplified from genomic DNA of a reference subject, which has been fragmented and/or labelled with a detectable label.

14. A method according to claim 1, wherein the measure of central tendency is selected from the group consisting of: the mean and the median.

15. A method according to claim 1, wherein said measured fluorescence signal is determined after trimming extreme readings.

16. A method according to claim 1, wherein said background fluorescence signal is determined after trimming extreme readings.

17. A method according to claim 1, wherein the genetic segment of interest comprises an exon of the human RHD gene.

18. A method according claim 17, wherein the oligonucleotide probes are selected from the probes shown in Table 4.

19. A method according to claim 18, wherein the method further comprises genotyping the test sample to identify at least one allele at a site of single nucleotide polymorphism ("SNP") in the human RHD gene.

20. A method for selecting at least one optimal probe set, the method comprising:
   (i) providing a plurality of candidate probe sets, each candidate probe set comprising a plurality of replicates of at least one oligonucleotide probe that interrogates a cognate sequence within a genetic segment of interest;
   (ii) bringing each of the candidate probe sets into contact with (a) a plurality of reference samples in which the genetic segment of interest is absent, and (b) a plurality of reference samples in which the genetic segment of interest is present, under conditions that allow probe-cognate sequence hybridisation to occur;
   (iii) measuring the intensity of probe-sample hybridisation of each of the reference samples, thereby obtaining for each candidate probe set a first cluster of hybridisation intensity values for the reference samples in which the genetic segment of interest is absent and a second cluster of hybridisation intensity values for the reference samples in which the genetic segment of interest is present; and
   (iv) scoring each of the candidate probe sets by dividing a measure of the interval between the first and second clusters by the sum of a measure of central tendency of the first and second clusters, thereby obtaining a probe set score for each of the candidate probe sets, wherein a higher probe set score indicates that the candidate probe set is more likely to be optimal for determining the presence or absence of the genetic segment of interest,
   wherein the reference samples are labelled with a fluorescent label and wherein the hybridisation intensity is measured as I/B, where:
   I is determined as a measure of central tendency of the measured fluorescence signal of the replicates of each oligonucleotide probe and
   B is determined as a measure of central tendency of the background fluorescence signal of the replicates of each oligonucleotide probe
and wherein the probe set score (S) for each candidate probe set is calculated according to the following formulae:

$$S = \frac{A}{M} = \frac{p(I/B)_1 - a(I/B)_n}{pMedian\ I/B + aMedian\ I/B}$$

where:
- aMedianI/B is a measure of central tendency of the measured I/B values of the reference samples in which the genetic segment of interest is absent;
- pMedianI/B is a measure of central tendency of the measured I/B values of the reference samples in which the genetic segment of interest is present;
- a(I/B)n is the greatest measured I/B value of the reference samples in which the genetic segment of interest is absent; and
- p(I/B)1 is the lowest measured I/B value of the reference samples in which the genetic segment of interest is present.

21. A method according to claim 1, wherein at least said first probe set is a probe set that has been selected using a method which comprises the following steps:
(i) providing a plurality of candidate probe sets, each candidate probe set comprising a plurality of replicates of at least one oligonucleotide probe that interrogates a cognate sequence within a genetic segment of interest;
(ii) bringing each of the candidate probe sets into contact with (a) a plurality of reference samples in which the genetic segment of interest is absent, and (b) a plurality of reference samples in which the genetic segment of interest is present, under conditions that allow probe-cognate sequence hybridisation to occur;
(iii) measuring the intensity of probe-sample hybridisation of each of the reference samples, thereby obtaining for each candidate probe set a first cluster of hybridisation intensity values for the reference samples in which the genetic segment of interest is absent and a second cluster of hybridisation intensity values for the reference samples in which the genetic segment of interest is present; and
(iv) scoring each of the candidate probe sets by dividing a measure of the interval between the first and second clusters by the sum of a measure of central tendency of the first and second clusters, thereby obtaining a probe set score for each of the candidate probe sets, wherein a higher probe set score indicates that the candidate probe set is more likely to be optimal for determining the presence or absence of the genetic segment of interest.

22. A method for determining a lower no call boundary ("LNC") and an upper no call boundary ("UNC") for at least a first probe set, the method comprising:
(i) bringing at least said first probe set comprising a plurality of replicates of at least one oligonucleotide probe that interrogates a first cognate sequence within a genetic segment of interest into contact with (a) a plurality of reference samples in which the genetic segment of interest is absent, and (b) a plurality of reference samples in which the genetic segment of interest is present;
(ii) measuring the intensity of probe-sample hybridisation of each of the reference samples, thereby obtaining a first cluster of hybridisation intensity values for the reference samples in which the genetic segment of interest is absent and a second cluster of hybridisation intensity values for the reference samples in which the genetic segment of interest is present; and
(iii) establishing a "no call" region of hybridisation intensity values that lies in the region between said first and second clusters and which is bounded by LNC and UNC, wherein the LNC and UNC represent statistical confidence limits for assigning a hybridisation intensity value to said first and said second clusters, respectively; wherein:
the DNA of the reference samples and/or the test sample has been labelled with a fluorescent label and wherein measuring hybridisation intensity comprises measuring the fluorescence signal of the fluorescent label at each oligonucleotide probe location;
the hybridisation intensity for each probe set is measured as I/B, where:
I is determined as a measure of central tendency of the measured fluorescence signal of the replicates of each oligonucleotide probe; and
B is determined as a measure of central tendency of the background fluorescence signal of the replicates of each oligonucleotide probe; and
the LNC and UNC values are calculated according to the following formulae:

$$L_{NC} = \frac{T_{I/B} \cdot [2 \cdot a(I/B)_n - aMedian\ I/B] - a(I/B)_n^2}{T_{I/B} - aMedian\ I/B}$$

$$U_{NC} = \frac{T_{I/B} \cdot [pMedian\ I/B - 2 \cdot p(I/B)_1] + p(I/B)_1^2}{pMedian\ I/B - T_{I/B}}$$

where:

$$T_{I/B} = \frac{pMedian\ I/B \cdot a(I/B)_n - aMedian\ I/B \cdot p(I/B)_1}{pMedian\ I/B + a(I/B)_n - aMedian\ I/B - p(I/B)_1}$$

aMedianI/B is a measure of central tendency of the measured I/B values of the reference samples in which the genetic segment of interest is absent;
pMedianI/B is a measure of central tendency of the measured I/B values of the reference samples in which the genetic segment of interest is present;
a(I/B)n is the greatest measured I/B value of the reference samples in which the genetic segment of interest is absent; and
p(I/B)1 is the lowest measured I/B value of the reference samples in which the genetic segment of interest is present.

23. A method for determining the presence or absence of a genetic segment of interest in a DNA-containing sample, the method comprising:
(i) bringing at least a first probe set comprising a plurality of replicates of at least one oligonucleotide probe that interrogates a first cognate sequence within said segment of interest into contact with at least one DNA-containing test sample under conditions that allow probe-cognate sequence hybridisation to occur;
(ii) measuring the intensity of probe-sample hybridisation of the at least one test sample; and
(iii) comparing the measured hybridisation intensity with a pre-determined lower no call boundary ("LNC") and a pre-determined upper no call boundary ("UNC"),
and wherein a measured hybridisation intensity below the LNC indicates that said genetic segment of interest is absent in the test sample and a measured hybridisation intensity above UNC indicates that said genetic segment of interest is present in the test sample, wherein said LNC and said UNC are determined by the method of claim 22.

24. A method according to claim 1, wherein said cognate sequence comprises a polymorphic site and wherein said first probe set comprises a plurality of replicates of at least two, at least three or at least four allele-specific oligonucleotide probes that distinguish the alleles of said polymorphic site.

25. A method according to claim 24, wherein said test sample comprises said genetic segment of interest, the method further comprising genotyping said test sample to identify an allele at said polymorphic site.

* * * * *